(12) United States Patent
Li et al.

(10) Patent No.: US 10,995,049 B2
(45) Date of Patent: May 4, 2021

(54) TOTAL SYNTHESIS OF PROSTAGLANDIN J NATURAL PRODUCTS AND THEIR INTERMEDIATES

(71) Applicant: California Institute of Technology, Pasadena, CA (US)

(72) Inventors: Jiaming Li, Pasadena, CA (US); Chen Xu, Guangdong (CN); Tonia S Ahmed, Pasadena, CA (US); Robert H Grubbs, South Pasadena, CA (US); Brian M. Stoltz, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/922,290

(22) Filed: Jul. 7, 2020

(65) Prior Publication Data

US 2021/0017111 A1    Jan. 21, 2021

Related U.S. Application Data

(60) Provisional application No. 62/876,531, filed on Jul. 19, 2019.

(51) Int. Cl.
| | | |
|---|---|---|
| *C07C 45/29* | (2006.01) | |
| *C07C 29/00* | (2006.01) | |
| *C07C 49/557* | (2006.01) | |
| *C07C 49/577* | (2006.01) | |

(52) U.S. Cl.
CPC ............ *C07C 45/29* (2013.01); *C07C 49/557* (2013.01); *C07C 49/577* (2013.01)

(58) Field of Classification Search
CPC ...... C07C 45/29; C07C 49/557; C07C 49/577
See application file for complete search history.

(56) References Cited

U.S. PATENT DOCUMENTS

| | | | |
|---|---|---|---|
| 6,552,139 B1 * | 4/2003 | Herrmann | C07C 6/04 526/171 |
| 6,635,768 B1 | 10/2003 | Herrmann et al. | |
| 6,787,620 B2 | 9/2004 | Herrmann et al. | |
| 7,094,898 B2 * | 8/2006 | Fogg | B01J 31/1616 546/4 |
| 7,294,717 B2 | 11/2007 | Herrmann et al. | |
| 7,378,528 B2 | 5/2008 | Herrmann et al. | |
| 7,652,145 B2 * | 1/2010 | Herrmann | B01J 31/2404 548/101 |
| 8,039,566 B2 | 10/2011 | Vougioukalakis et al. | |
| 8,362,311 B2 | 1/2013 | Schrock et al. | |
| 8,546,500 B2 | 10/2013 | Hoveyda et al. | |
| 8,598,400 B2 | 12/2013 | Hoveyda et al. | |
| 8,716,488 B2 | 5/2014 | Jensen et al. | |
| 9,073,801 B2 | 7/2015 | Hoveyda et al. | |
| 9,079,173 B2 | 7/2015 | Schrock et al. | |
| 9,085,595 B2 | 7/2015 | Hoveyda et al. | |
| 9,206,211 B2 | 12/2015 | Schrock et al. | |
| 9,303,100 B2 | 4/2016 | Jensen et al. | |
| 9,315,604 B2 | 4/2016 | Schrock et al. | |
| 9,409,938 B2 | 8/2016 | Schrock et al. | |
| 9,441,059 B2 | 9/2016 | Schrock et al. | |
| 9,446,394 B2 | 9/2016 | Hoveyda et al. | |
| 9,457,347 B2 | 10/2016 | Jensen et al. | |
| 9,586,981 B2 | 3/2017 | Herbert et al. | |
| 9,676,676 B2 | 6/2017 | Hartung et al. | |
| 9,701,702 B2 | 7/2017 | Schrock et al. | |
| 9,713,808 B2 | 7/2017 | Schrock et al. | |
| 9,771,386 B2 | 9/2017 | Hoveyda et al. | |
| 9,795,953 B2 * | 10/2017 | Jensen | C07C 2/02 |
| 9,850,268 B2 | 12/2017 | Hoveyda et al. | |
| 9,919,299 B2 | 3/2018 | Ondi et al. | |
| 9,920,086 B2 | 3/2018 | Lund et al. | |
| 9,938,253 B2 * | 4/2018 | Hoveyda | B01J 31/2273 |
| 10,072,036 B2 | 9/2018 | Buchmeiser et al. | |
| 10,106,566 B2 | 10/2018 | Toth et al. | |
| 10,173,208 B2 | 1/2019 | Schrock et al. | |
| 10,265,691 B2 | 4/2019 | Jensen et al. | |
| 10,343,153 B2 | 7/2019 | Varga et al. | |
| 2020/0102285 A1 | 4/2020 | Ahmed et al. | |

FOREIGN PATENT DOCUMENTS

WO    20191222244 A1    11/2019

OTHER PUBLICATIONS

Li et al. Concise Syntheses of Delta-12 Prostaglandin J Natural Products via Stereoretentive Metathesis. Journal of the American Chemical Society, vol. 141, 154-158. (Year: 2018).*

Xu et al. In Situ Methylene Capping: A General Strategy for Efficient Stereoretentive Catalytic Olefin Metathesis. The Concept, Methodological Implications, and Applications to Synthesis of Biologically Active Compounds. Journal of the American Chemical Society, vol. 139, 10919-10928. (Year: 2017).*

Bickley et al. Synthesis of Optically Active Prostaglandin-J2 and 15-Deoxy-delta 12, 14-prostaglandin-J2. Synlett, No. 8, 1170-1174. (Year: 2003).*

Acharya et al. Highly efficient total synthesis of delta-12 PGJ2, 15-deoxy-delta 12, 14-PGJ2, and their analogues. Tetrahedron, vol. 62, 3329-3343. (Year: 2006).*

(Continued)

*Primary Examiner* — Sikarl A Witherspoon
(74) *Attorney, Agent, or Firm* — BakerHostetler

(57) ABSTRACT

The present disclosure is directed to methods of preparing prostaglandin J natural products by stereoretentive metatheses reactions and intermediates used in the synthesis of these natural products, including the use of intermediates of Formula (I-A), where $R^1$ is defined in the specification

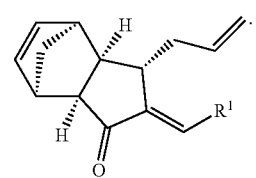

12 Claims, 12 Drawing Sheets

(56) References Cited

OTHER PUBLICATIONS

Nicolaou eta.. Short Total Synthesis of delta-12-Prostaglandin J2 and Related Prostaglandins. Design, Synthesis, and Biological Evaluation of Macrocyclic delta-12-Prostaglandin J2 Analogues. Journal of Organic Chemistry, vol. 84, 365-378. (Year: 2019).*
Acharya, H.P., et al., Tetrahedron Lett., 2004, 45,1199-1202.
Ahmed, T. S, et al., Angew. Chem., Int. Ed. 2017, 56, 11213-11216.
Ahmed, T. S., et al., J. Am. Chem. Soc. 2017, 139, 1532-1537.
Ahmed, T. S., etal., Chem. Sci. 2018, 9, 3580-3583.
Brummond, K. M, et al., Org. Lett. 2004, 6, 149-152.
Chang, X., etal., Org. Lett. 2019, 21, 1191-1196.
Couturier, J.-L., et al., Int. Ed. Engl. 1992, 31, 628-631.
Eddolls, J. P., etal., Tetrahedron 2004, 60, 2539-2550.
Egger, J., etal., Org. Lett. 2015, 17, 4340-4343.
Endo., K., etal., J. Am. Chem. Soc. 2011, 133, 8525.
Grieco, P. A., et al., J. Org. Chem. 1989, 54, 6008-6010.
Hoover, J. M., et al., J. Am. Chem. Soc. 2011, 133, 16901-16910.
Hoveyda, A. H. , J. Org. Chem. 2014, 79, 4763-4792.
Iqbal, M., et al., Tetrahedron Lett., 2003, 44, 5741-5745.
Iqbal, M., et al., Tetrahedron, 2004, 60, 2531-2538.
Iqbal, M., etal., Org. Biomol. Chem. 2008, 6, 4649-4661).
Johns, A. M., etal., Org. Lett. 2016, 18, 772-775.
Jung, K., etal., Macromolecules 2018, 51, 4564-4571.
Karki, K., etal., Synlett 2018, 29, 1723-1728.
Keitz, B. K., et al., Am. Chem. Soc. 2011, 133, 9686.
Keitz, B. K., etal., J. Am. Chem. Soc. 2012, 134, 2040.
Keitz, B. K., etal., J. Am. Chem. Soc. 2012, 134, 693.
Khan, R. K. M. , et al., J. Am. Chem. Soc. 2013, 135, 10258-10261.
Kim, N.-J., et al., J. Org. Chem. 2010, 75, 7458-7460.
Kobayashi et al., J. Org. Chem. 2002, 67, 7110-7123.
Koh, M. J, et aL, Angew. Chem., Int. Ed. 2014, 53, 1968-1972.
Koh, M. J., et al., Nature 2017, 542, 80-85.
Koh, M. J., etal., Nature 2015, 517, 181-186.
Lam, J. K., et al., J. Am. Chem. Soc. 2016, 138, 15774-15783.
Mehta, G., et al., Tetrahedron Lett. 1999, 40, 991-994.
Mihelich, E. D., et aL, J. Org. Chem. 1983, 48, 4135-4137.
Montgomery, T. P., et al., Angew. Chem., Int. Ed. 2017, 56, 11024-11036.
Nguyen, T. T., etaL, Science 2016, 352, 569-575.
Nicolaou, K. C., Chem.-Eur. J. 2016, 22, 8559-8570.
Nicolaou, K. C., et al., Angew. Chem., Int. Ed. 2014, 53, 10443-10447.
Orgue, S., et al., Org. Lett. 2015, 17, 250-253.
Pelss, A., etal. Chem.-Eur. J. 2018, 24, 9542-9545.
Rosebrugh, L. E. et al., J. Am. Chem. Soc., 2013, 135, 1276-1279.
Shen, X., et al., Nature 2017, 541, 380-385.
Tanaka, K., et al., Synthesis 1995, 1995, 1237-1239.
Verdaguer, X., et al., J. Org. Chem. 2004, 69, 8053-8061.

* cited by examiner

Z-selective methathesis catalysts:

Stereoretentive methathesis catalysts:

FIG. 5B, continued
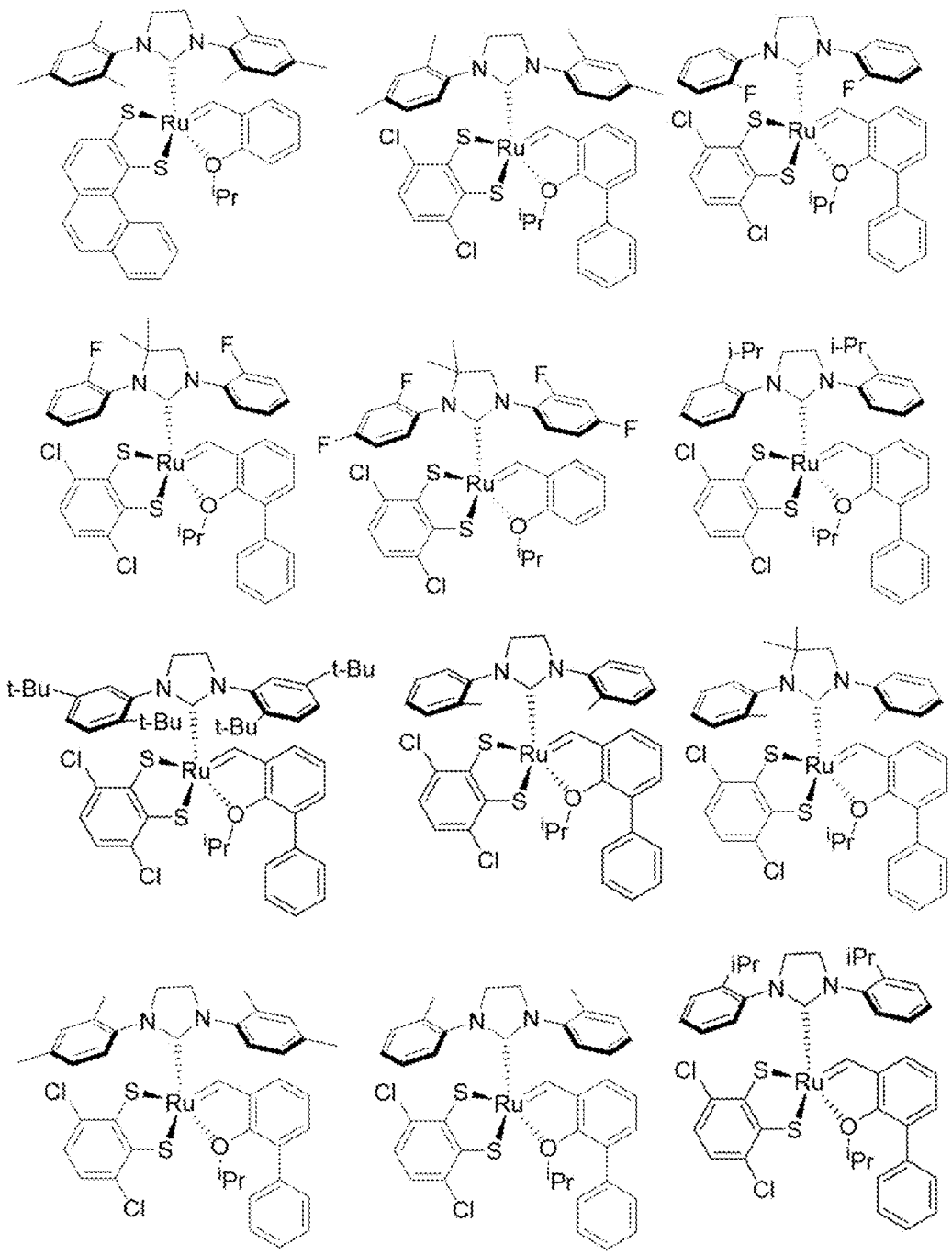

FIG. 5B, continued
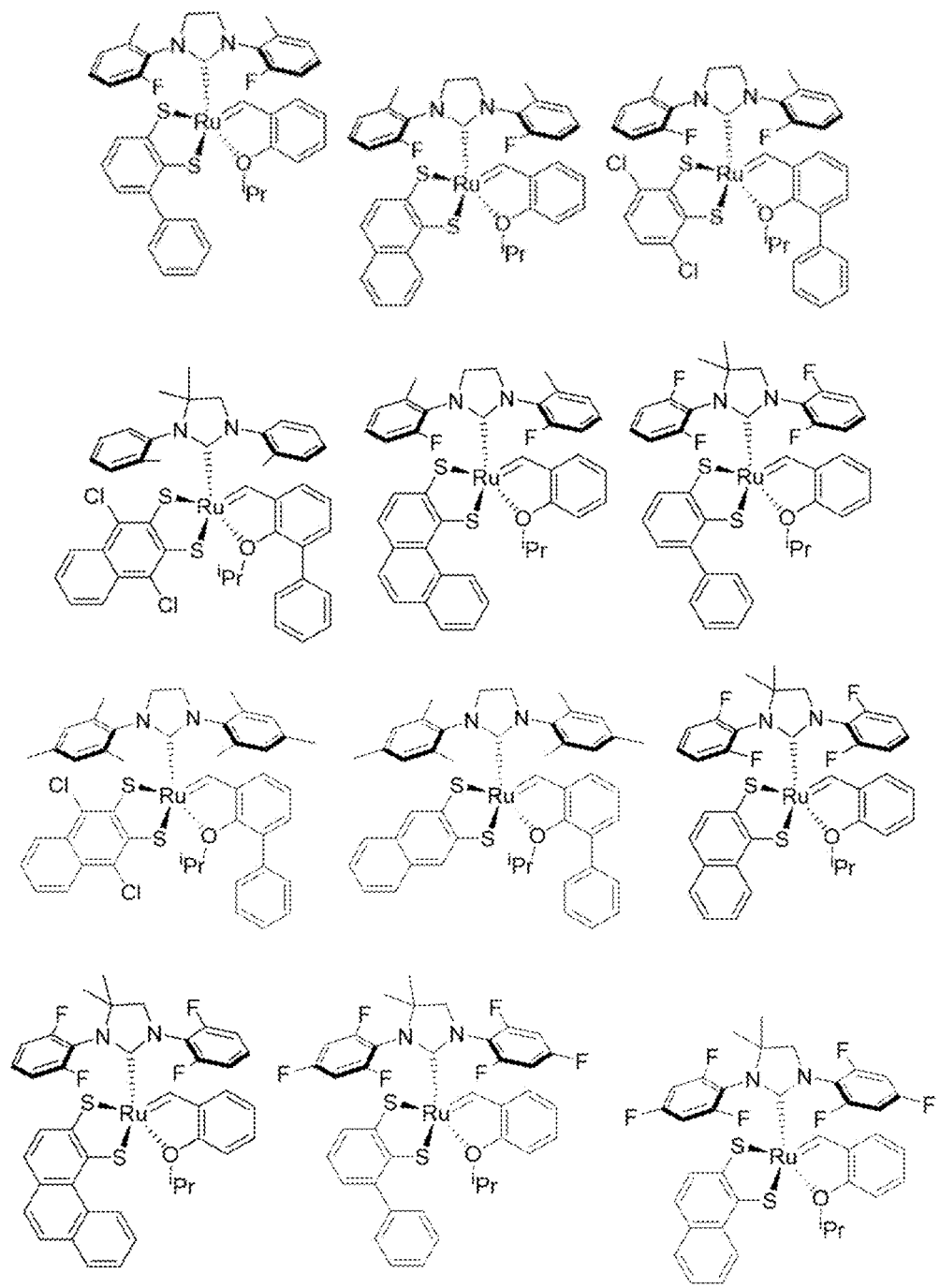

FIG. 5B, continued
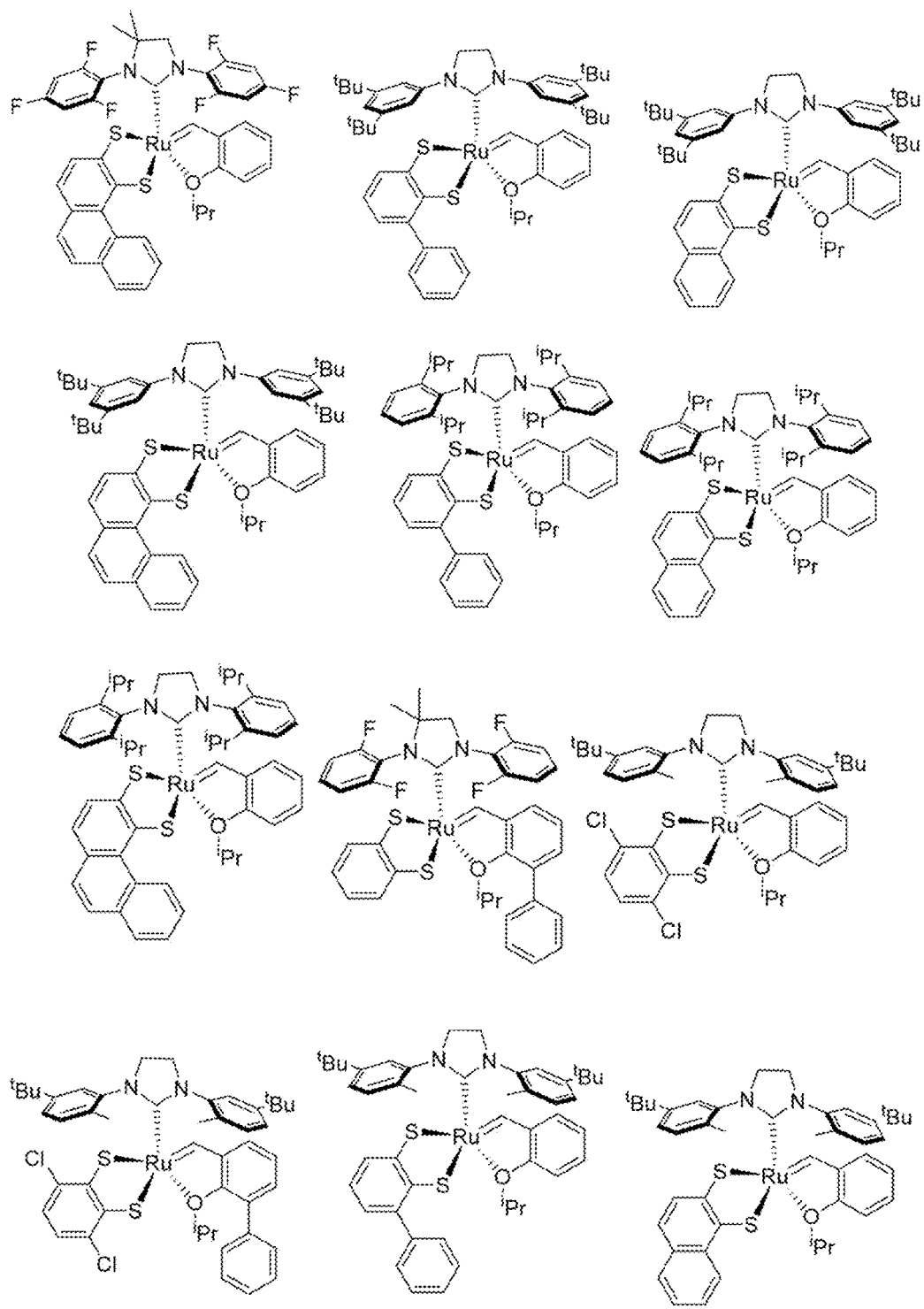

FIG. 5B, continued
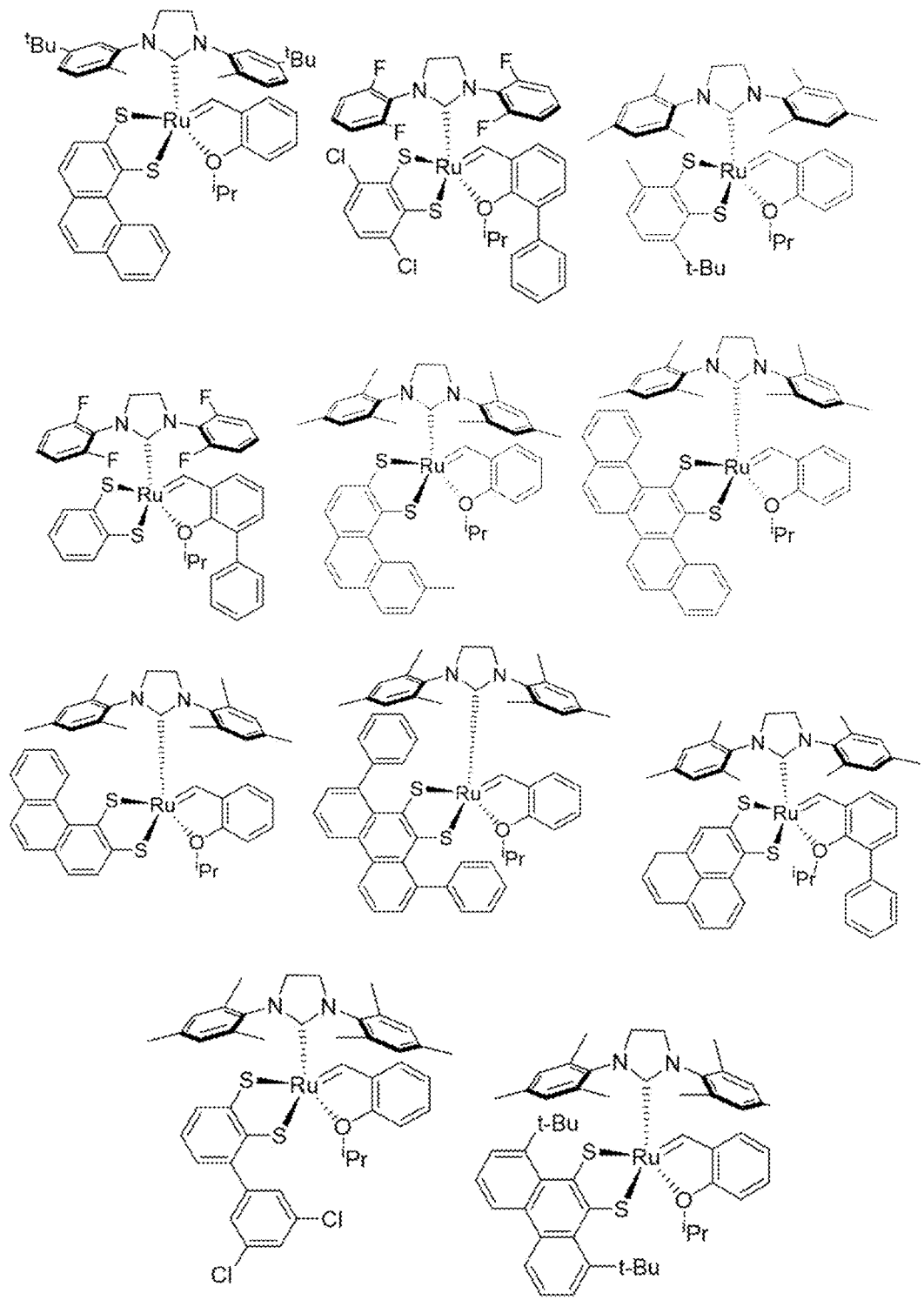

TOTAL SYNTHESIS OF PROSTAGLANDIN J NATURAL PRODUCTS AND THEIR INTERMEDIATES

CROSS REFERENCE TO RELATED APPLICATIONS

This application claims priority to U.S. Patent Application No. 62/876,531, filed Jul. 19, 2019, the contents of which are incorporated by reference herein for all purposes

GOVERNMENT RIGHTS

This invention was made with government support under Grant No. GM031332 awarded by the National Institutes of Health. The government has certain rights in the invention.

TECHNICAL FIELD

The present disclosure is directed to methods of preparing prostaglandin J natural products by stereoretentive metatheses reactions and intermediates used in the synthesis of these natural products.

BACKGROUND $\Delta^{12}$-prostaglandin J natural products (1-4, FIG. 1) features a unique cross-conjugated dienone motif and appealing anti-cancer activity. $\Delta^{12}$-PGJs are secondary metabolites of fatty acids (ARA or EPA), isolated from cell culture. For example, ω-6 arachidonic acid (ARA) is converted by cyclooxygenase (COX; also known as PGH synthase) to PGH2. This pivotal intermediate is converted enzymatically to a variety of biologically active prostaglandins, including $PGD_2$, $PGE_2$, $PGF_{2\alpha}$, and $PGI_2$. $PGD_2$ can be spontaneously converted to $\Delta 12\text{-}PGJ_2$ and $15d\text{-}PGJ_2$ via a nonenzymatic process. A similar biosynthetic pathway is known to account for the formation of $\Delta 12\text{-}PGJ_3$ and $15d\text{-}PGJ_3$ from ω-3 eicosapentaenoic acid (EPA). Among the Δ12-prostaglandin J family, 15d-PGJ2 is the most well-studied and it is reported to be an endogenous ligand for peroxisome proliferator activated receptor-γ (PPAR-γ), which recognizes PPAR-response elements (PPRE) in the promoter region of target genes to stimulate or suppress DNA transcription. This pathway is responsible for the antineoplastic, anti-inflammatory, antiviral, and antiproliferative properties of 15d-PGJ2. Recently, it was reported that selenium supplementation upregulated the ARA metabolism to favor the production of CyPGs, which resulted in an amplification of PPAR-γ signaling, inhibiting chronic myeloid leukemia (CML) progression. 15d-PGJ2 features a unique cross-conjugated dienone motif, and this highly electrophilic structure accounts for the modifications of many proteins by covalent interactions. For example, crystallographic data show that PPAR-γ is covalently modified by 15d-PGJ2 via a Michael addition at the C9 or C13 position with the cysteine C285 residue.

Synthetic efforts toward $\Delta^{12}$-prostaglandin J compounds began in 2003, with a number of syntheses of $\Delta^{12}$-PGJ$_2$ (see FIG. 1) and 15d-PGJ$_2$ (see FIG. 1) reported through various approaches. See, e.g., (a) Bickley, J. F., et al., *Synlett* 2003, 1170-1174; (b) Brummond, K. M, et al., *Org. Lett.* 2004, 6, 149-152; (c) Acharya, H. P., et al., *Tetrahedron Lett.* 2004, 45, 1199-1202; (d) Acharya, H. P., et al., *Tetrahedron* 2006, 62, 3329-3343; (e) Kim, N.-J., et al., *J. Org. Chem.* 2010, 75, 7458-7460; (f) Egger, J., et al., *Org. Lett.* 2015, 17, 4340-4343; (g) Nicolaou, K. C. et al, *J. Org. Chem.* 2019, 84, 365-378. Total synthesis of $\Delta^{12}$-PGJ$_3$ (see FIG. 1) were reported by Nicolaou and co-workers (see, e.g., (a) Nicolaou, K. C., et al., *Angew. Chem., Int. Ed.* 2014, 53, 10443-10447; (b) Nicolaou, K. C., *Chem.-Eur. J.* 2016, 22, 8559-8570 and more recently by the Aggarwal group (see, e.g., Pelšs, A., et al.. *Chem.-Eur. J.* 2018, 24, 9542-9545.).

Recently, Grubbs and Stoltz labs developed the shortest synthesis of all four of the $\Delta^{12}$-PGJ natural products by using stereoretentive metathesis. See WO2019222244 and Li, Jiaming, et al., "Concise Syntheses of $\Delta^{12}$-Prostaglandin J Natural Products via Stereoretentive Metathesis," *J. Amer. Chem. Soc.* 2019, 141, 154-158, each of which are incorporated by reference for all their teachings with respect to the methods and strategies for preparing prostaglandins and their intermediates. For example, tandem conjugate addition, aldol reaction and dehydration was performed to obtain 9, (references to compounds in this section are directed to those in FIG. 2), which was subjected to the standard one-pot stereoretentive homodimerization/cross-metathesis conditions. 10 was obtained in excellent yield (93% yield, FIG. 2) with high Z-selectivity (>99% Z). Finally, Ley oxidation of 10 gave 15-deoxy-$\Delta^{12,14}$-prostaglandin J$_2$ (FIG. 2) in 68% yield.

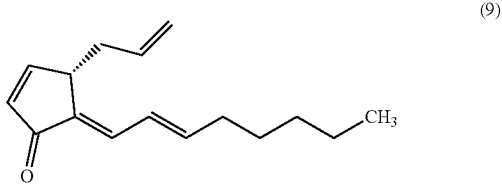 [SMILES: C=CC[C@H]1C=CC(=O)/C1=C/C=C/CCCCC]

(9)

However, intermediate 9 was obtained with a substantial loss in enantiopurity (88% ee) from enantiopure starting material 1 (>99% ee). The metathesis product 10 was obtained without significant erosion of enantiopurity (87% ee), which indicated that stereoretentive metathesis with the Z-selective ruthenium catalyst (designated "Ru-4," vida infra) retained the stereochemistry of the C8 stereocenter. Since the enantioenriched product is highly desirable in the downstream applications, such as in pharmaceutical industry, the inventors embarked on a study aimed to improve the enantioselectivity as well as the overall yield of intermediate 9.

The present disclosure sets forth the results of these exhaustive investigation that address at least some of these issues, as relevant to this and other such intermediates.

SUMMARY

The present disclosure sets forth synthetic schemes, intermediates, and associated steps for the improved syntheses of prostaglandin J natural products. Generally, the independent steps may be seen as comprising the novel use of a 3-oxodicyclopendadiene as a starting material, enzymatic kinetic resolution of that 3-oxodicyclopendadiene to introduce the high enantiopure chirality, a subsequent three-component coupling, and a retro-Diels-Alder reaction to give rise to an enantioenriched intermediate, set forth below as Formula (I-A) or (I-B) (see also Intermediate 6 in FIG. 2). Key improvement included the increased yield of this intermediate, higher enantiopurity without racemization, and better scalability. These steps are seen to be scalable to large-scale process of the $\Delta^{12}$-prostaglandin Js and their analogs as active pharmaceutical ingredients. Further, the schemes and methods are also applicable to the formation of other related prostaglandin J intermediates.

In this context, the present disclosure sets forth at least the following compounds and processes.

Certain embodiments of the present disclosure set forth compounds of the general Formula (I) or its enantiomers Formula (I-A) and/or (I-B):

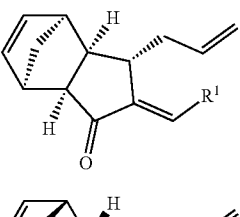
(I)

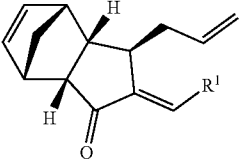
(I-A)

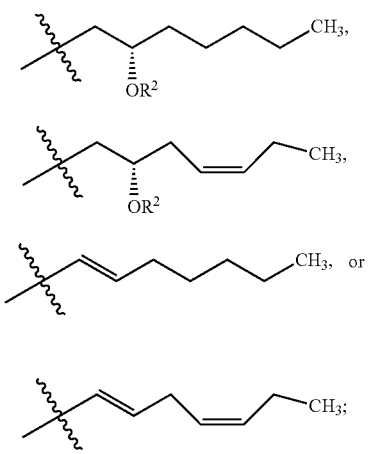
(I-B)

where $R^1$ is one of (P-1), (P-2), (P-3), or (P-4):

(P-1)

(P-3)

(P-2)

(P-4)

$R^2$ is H or an alcohol protecting group.

The depictions of Formula (I-A) and (I-B) refer to enantiomerically enriched or preferably enantiopure isomers, and the compounds of Formula (I) represent racemic mixtures thereof. The "A" and "B" designations are used as such throughout this disclosure.

This disclosure also sets forth these compounds and methods for making these intermediates, in racemic, enantioenriched, and enantiopure (>99% ee) forms. For examples, certain embodiments set forth herein include those methods of making a compound of Formula (I) (and its enriched enantiomers of nominal Formula (I-A) and (I-B)) by coupling an allyl group and an ω-chain to a compound of Formula (II),

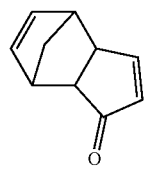
(II)

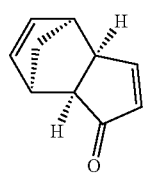
(II-A)

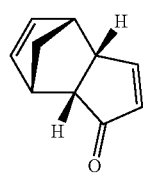
(II-B)

for example by selective conjugate addition of an allyl group using an organocopper allyl source and trapping the resulting enolate by subsequent addition of an aldehyde of Formula (O-1), (O-2), (O-3), or (O-4):

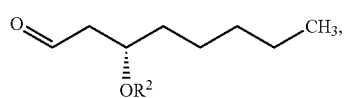
(O-1)

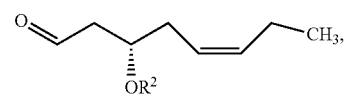
O-3)

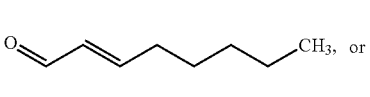
(O-2)

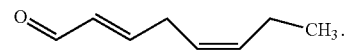
O-4)

This trapping results in the formation of an aldol intermediate that can be oxidized to form the respective compound of Formula (I).

Other embodiments provide improved methods for resolving the enantiomers of Formula (II-A) and (II-B).

In other independent embodiments, the compounds of Formula (I), or their enriched enantiomers Formula (IA) or (I-B) serve as useful precursors for the downstream reactions to form prostaglandin J natural products (or their protected derivatives) by steps which include the stereoretentive formation of the cyclopentenone ring structure and Z-selective or stereoretentive metathesis of the allyl group to form a Z-enriched olefin as is characteristic of these prostaglandin materials. These steps, which include the use of retro-Diels Alder and Z-selective or stereoretentive metathesis reactions can be independently applied in either order. For example, as shown schematically for one set of enantiomers:

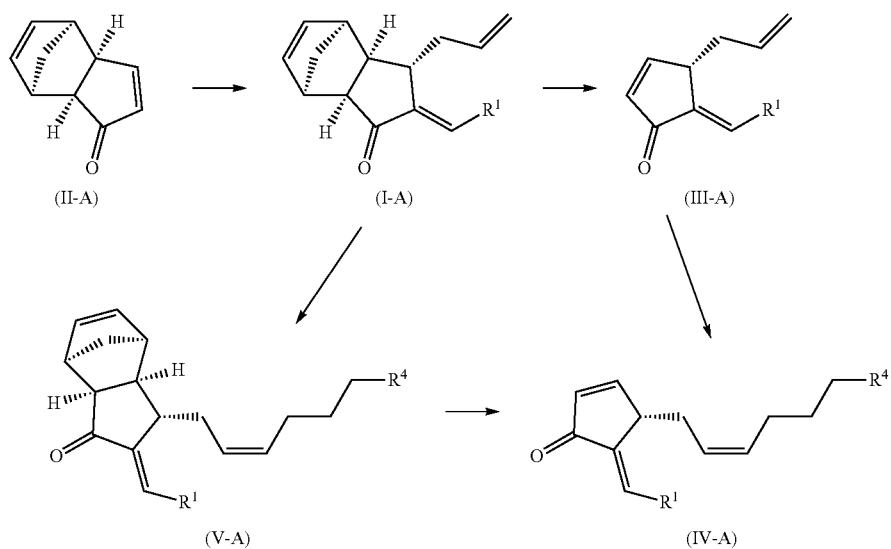

For example, certain embodiments provide for the conversion of compounds of Formula (I), (I-A), and/or (I-B) to compounds of Formula (III), (III-A), and/or (III-B), respectively.

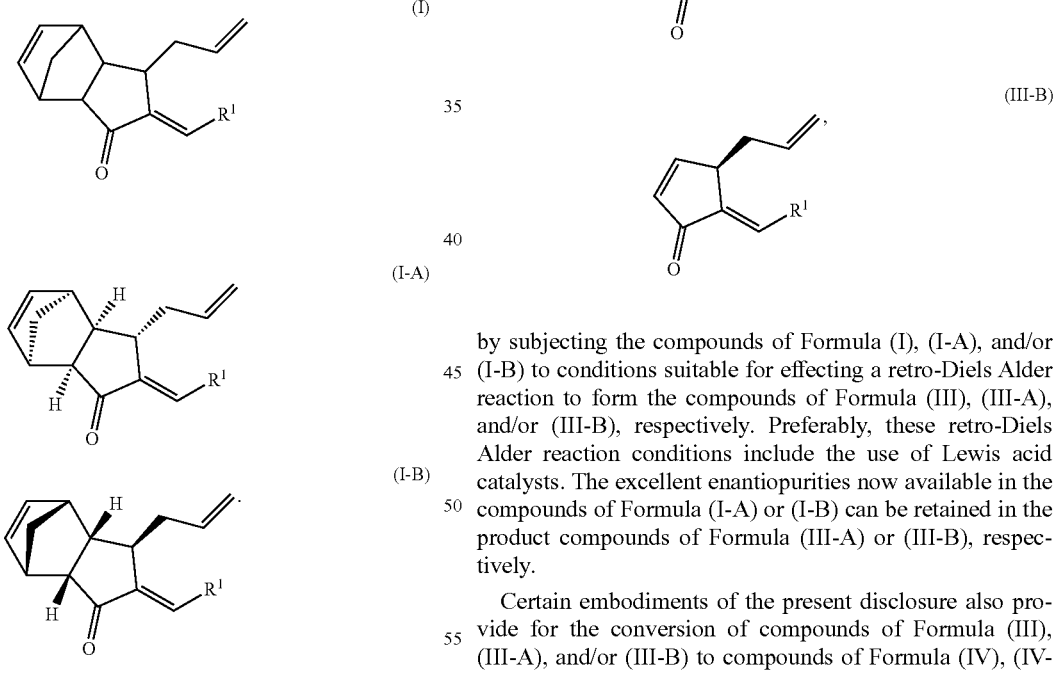

by subjecting the compounds of Formula (I), (I-A), and/or (I-B) to conditions suitable for effecting a retro-Diels Alder reaction to form the compounds of Formula (III), (III-A), and/or (III-B), respectively. Preferably, these retro-Diels Alder reaction conditions include the use of Lewis acid catalysts. The excellent enantiopurities now available in the compounds of Formula (I-A) or (I-B) can be retained in the product compounds of Formula (III-A) or (III-B), respectively.

Certain embodiments of the present disclosure also provide for the conversion of compounds of Formula (III), (III-A), and/or (III-B) to compounds of Formula (IV), (IV-A), and/or (IV-B), respectively:

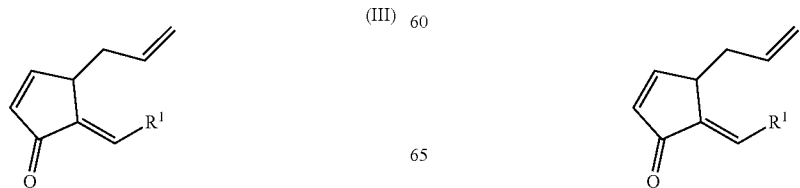

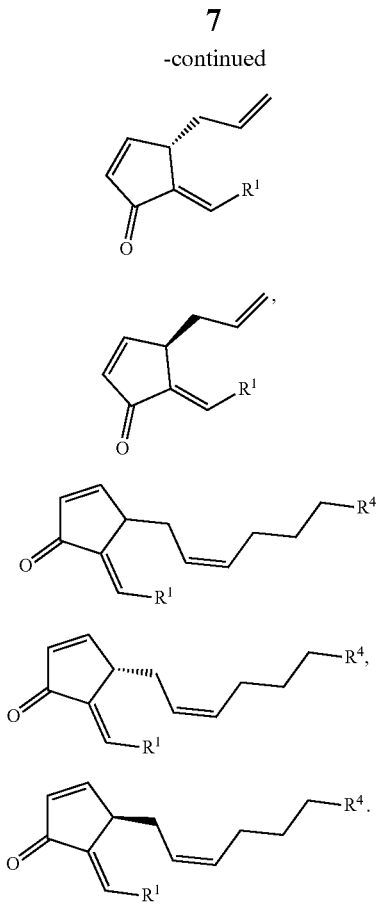

(III-A)

(III-B)

(IV)

(IV-A)

(IV-B)

by reacting the compounds of Formula (III), (III-A), and/or (III-B) with a compound of Formula (ZO-1) or preferably (ZO-2), in the presence of a Group 6 or Group 8 metal Z-selective or stereoretentive olefin metathesis catalyst:

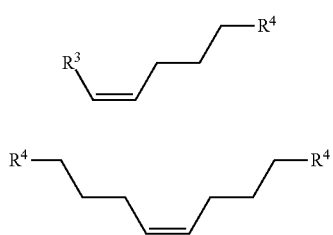

(ZO-1)

(ZO-2)

where $R^3$ is H or a $C_{1-3}$alkyl, preferably a C1 or C2 alkyl;

$R^4$ is independently $CH_2$—$OR^2$, an optionally protected carboxylate (—COOH) (that includes ester and amides), optionally protected aldehyde (—CHO), or a cyano (—CN);

to form the compound of Formula (IV), (IV-A) or (IV-B), respectively.

In preferred embodiments, the Z-selective or stereoretentive olefin metathesis catalyst and the associated metathesis reaction conditions provide for the formation of the cis-olefin having a Z/E selectivity of at least 90/10, at least 95/5, at least 96/4, at least 97/3, at least 98/2, at least 99/1, at least 99.5/0.5, or practically 100/0. In some embodiments, the Z-selective or stereoretentive olefin metathesis catalyst is a Z-selective or stereoretentive Grubbs ruthenium metathesis catalyst. In some other embodiments, the Z-selective or stereoretentive olefin metathesis catalyst is a Z-selective or stereoretentive Schrock tungsten or molybdenum olefin metathesis catalyst.

In some embodiments, the compounds of Formula (I), (I-A), and/or (I-B) are subjected to Z-selective or stereoretentive olefin metathesis conditions as set forth above to form the compounds of Formula (V), (V-A), and/or (V-B), and then subjecting these intermediates to the retro-Diels Alder reaction conditions to form the compounds of Formula (IV), (IV-A), and/or (IV-B) under the same or similar conditions described for each of these steps.

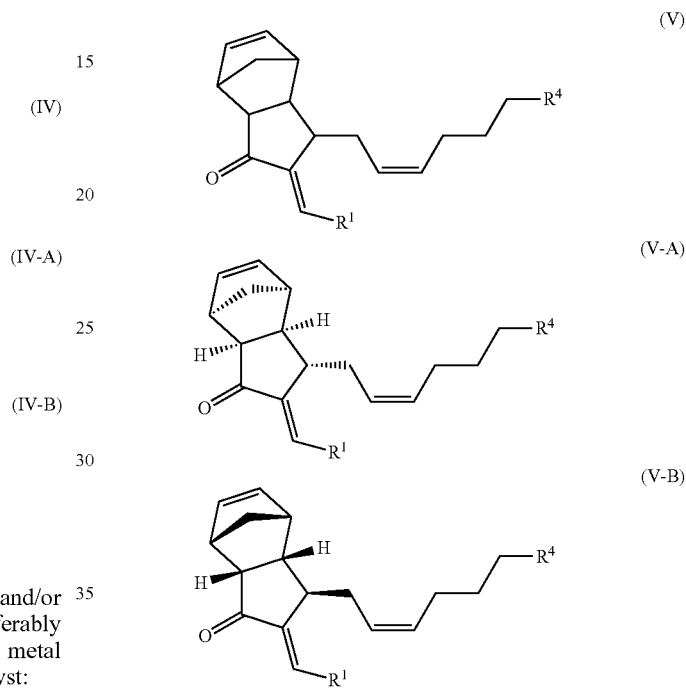

Once prepared, the compounds of Formula (IV), (IV-A), and/or (IV-B) can be converted to their corresponding prostaglandin J natural products of Formula (VI), (VI-A), and/or (VI-B), or derivatives thereof, by known methods.

Each of these transformations (e.g., (II)=>(I), (I)=>(III), (III)=>(IV), (I) >(V), or (V)=>(IV)) may be considered individually, though processes including two or more of these steps in combination are seen as independent embodiments.

BRIEF DESCRIPTION OF THE DRAWINGS

The present application is further understood when read in conjunction with the appended drawings. For illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

(FIG. 3). The acidity of the enone γ-position (and the tendency for racemization) can be reduced by interrupting the conjugation of the 7-system in these masked forms. The retro-Diels-Alder reaction presented itself as a desirable approach since the 3-oxodicyclopentadiene starting material was readily available.

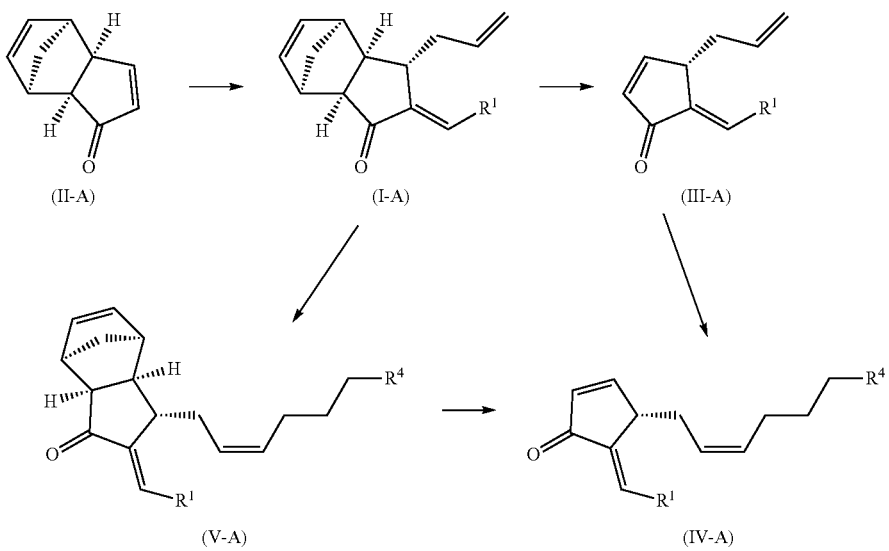

Figure 9:
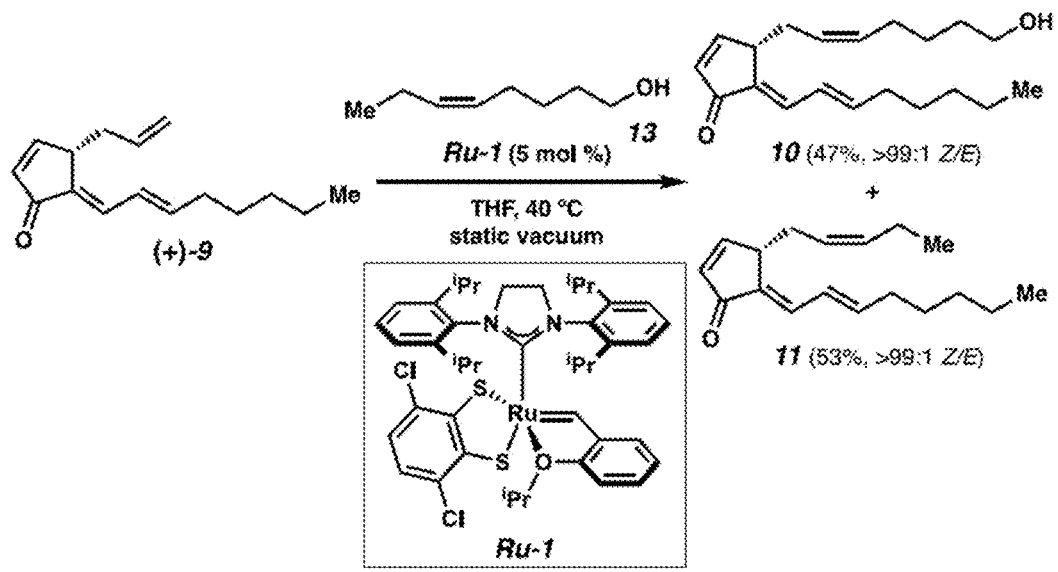
Figure 9:
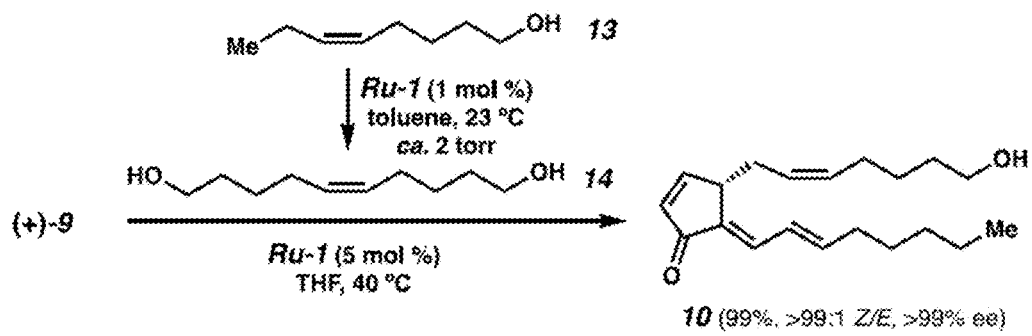

FIG. 9 presents synthetic schemes for stereoretentive metathesis reactions with (+)-9.

Figure 10:
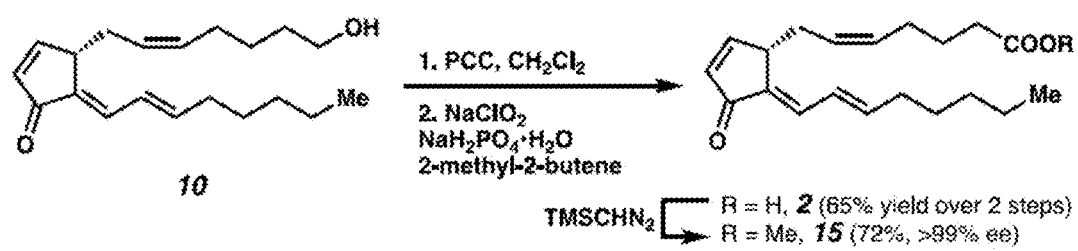

FIG. 10 shows synthetic schemes of 15d-PGJ$_2$ and 15d-PGJ$_2$ methyl ester

DETAILED DESCRIPTION OF ILLUSTRATIVE EMBODIMENTS

The present disclosure is directed to intermediates, including known intermediates having previously unavailable enantiopurities, useful in the preparation of prostaglandin J natural products, the methods of making these intermediates, and the methods of using these intermediates to prepare the prostaglandin J natural products.

As set forth above, previous methods resulted in a substantial loss of enantiopurity during the coupling of the hydrocarbon "arms" to the cyclopent-2-en-3-one ring system. In seeking to address this deficiency, the present inventors embarked on a substantial study in an effort to overcome this issue. During the course of these studies, the inventors recognized that the racemization of the relatively acidic C8 stereocenter of the reactive 2-alkylidene cyclopentenone moiety may have been responsible for this loss of enantiopurity. In order to prevent racemization, several approaches that used masked forms of this structural motif. The inventors considered schemes involving "masked" enone precursors, in which the enone could then be unmasked at the late stage of the syntheses using a retro-Diels-Alder reaction (for example, Iqbal, M., et al., *Tetrahedron* 2004, 60, 2531-2538; Iqbal, M., et al., *Tetrahedron Lett.*, 2003, 44, 5741-5745; Eddolls, J. P., et al., *Tetrahedron* 2004, 60, 2539-2550; Iqbal, M., et al., *Org. Biomol. Chem.* 2008, 6, 4649-4661), a Saegusa-Ito oxidation (for example, Kim, N.-J.; Moon, H., et al., *J. Org. Chem.* 2010, 75,

General Embodiments

Certain embodiments of the present disclosure include those compounds of the Formulae (I), (II), (III), (IV), (V), and (VI), and their enantiomer-rich compositions designated Formula (I-A)/(I-B), Formula (II-A)/(II-B), Formula (III-A)/(III-B), Formula (IV-A)/(IV-B), Formula (V-A)/(V-B), and Formula (VI-A)/(VI-B), respectively:

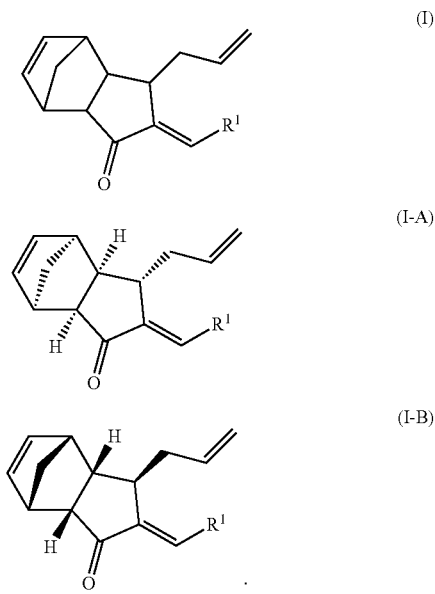

-continued
(II)
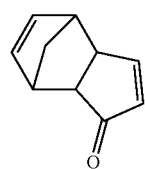
(II-A)
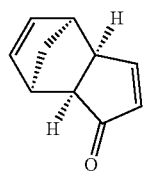
(II-B)
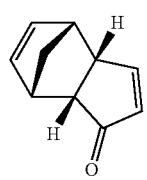
(III)
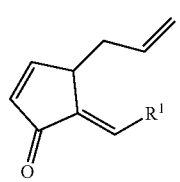
(III-A)
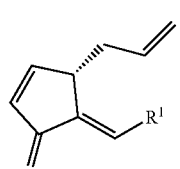
(III-B)
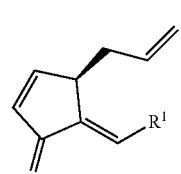
(IV)
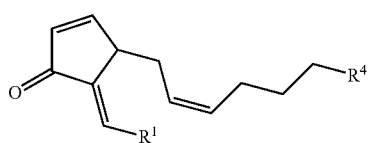
(IV-A)
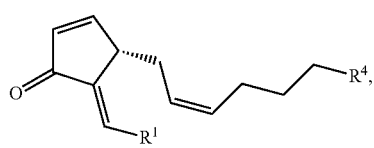
(IV-B)
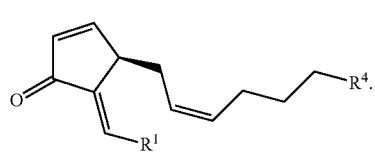
-continued
(V)
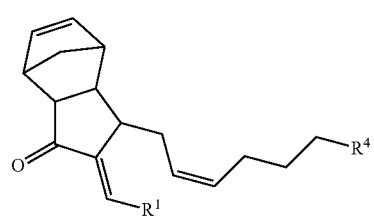
(V-A)
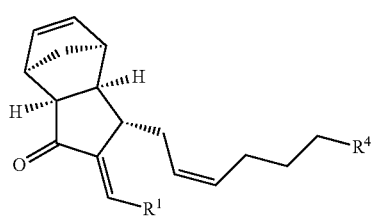
(V-B)
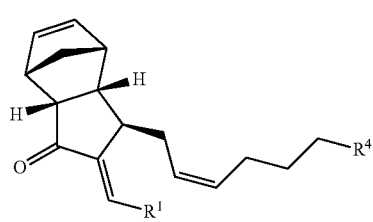
(VI)
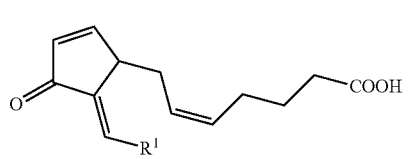
(VI-A)
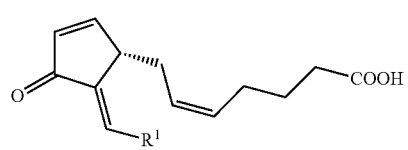
(VI-B)
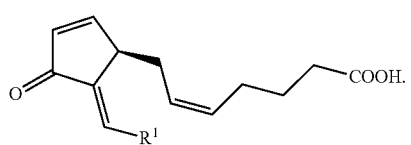
In the context of these compositions:
$R^1$ is one of (P-1), (P-2), (P-3), or (P-4):
(P-1)
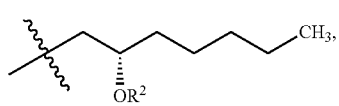
(P-2)
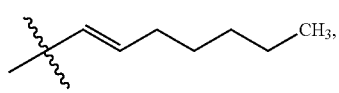
(P-3)
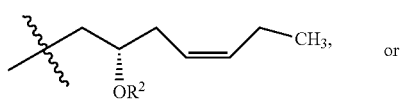
or -continued

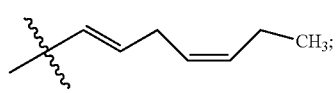
(P-4)

and

R² is independently H or an alcohol protecting group. Such alcohol protecting groups are known. Such protecting groups, plus a detailed description of techniques useful in adding and removing these of protecting groups are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for all purposes, or at least for their teaching of protecting groups and the methods of adding and removing them.

The compositions of Formula (I), (I-A), and (I-B) may be represented more specifically as

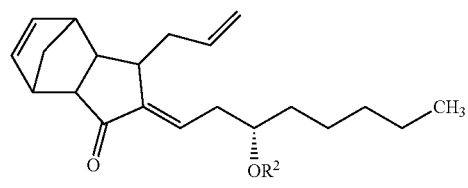

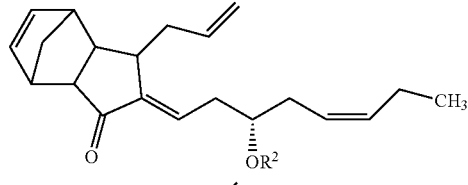

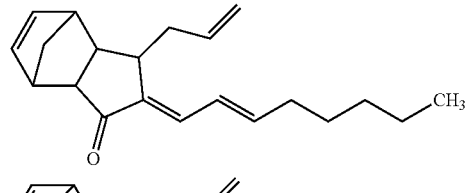

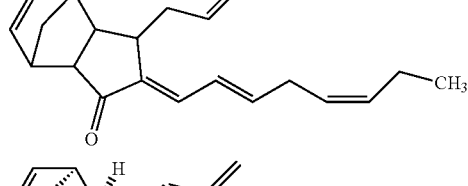

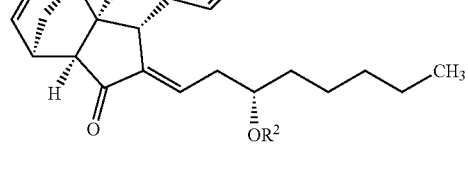

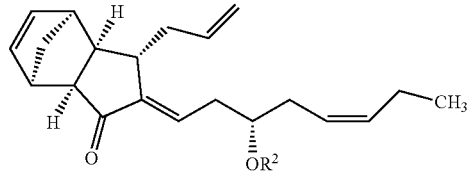

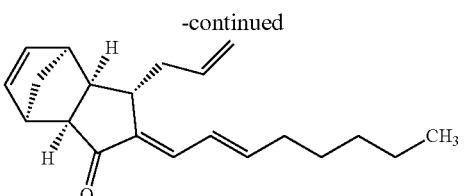

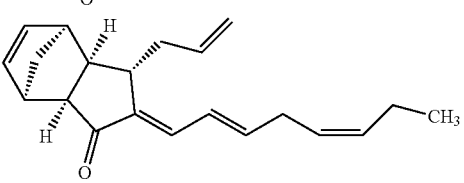

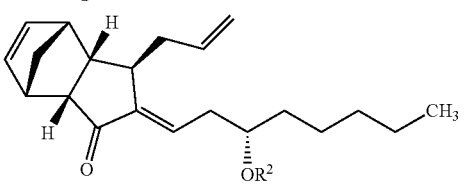

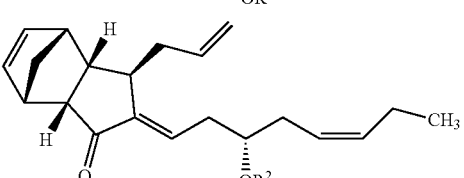

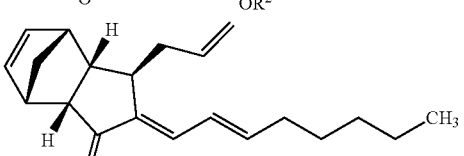

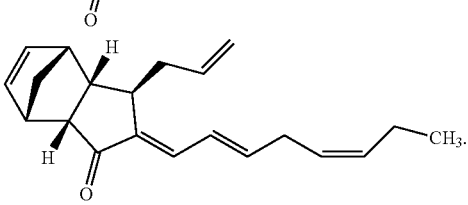

The compositions of Formula (III), (III-A), and (III-B) may be represented more specifically as:

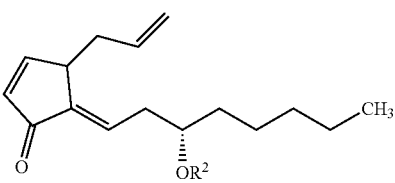

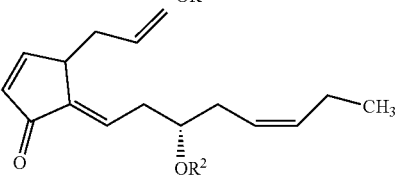

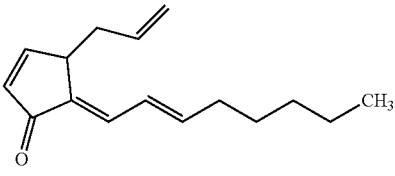

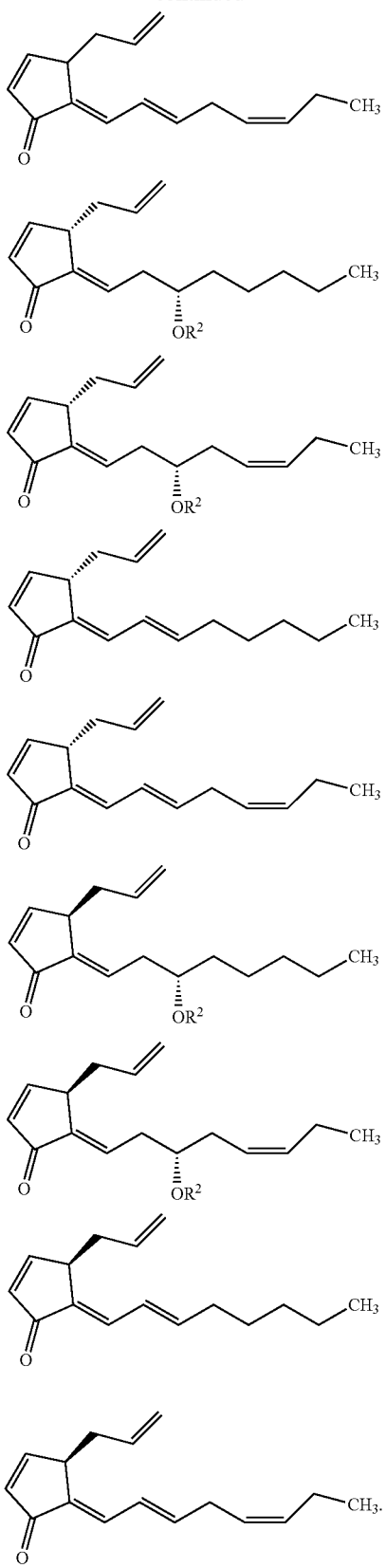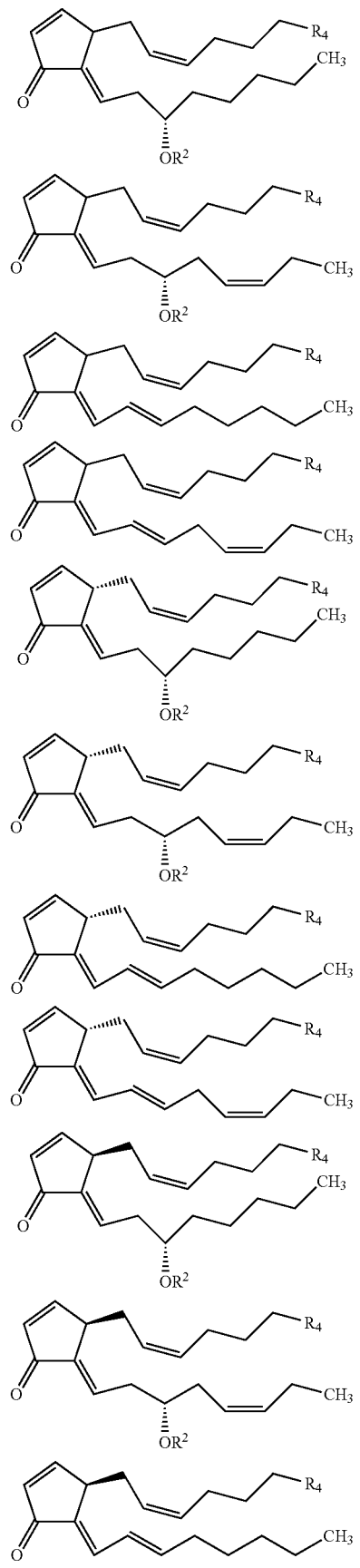
The compositions of Formula (IV), (IV-A), and (IV-B) may be represented more specifically as:

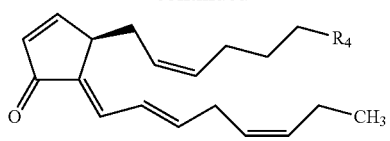
The compositions of Formula (V), (V-A), and (V-B) may be represented more specifically as:
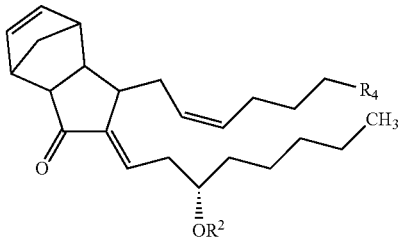
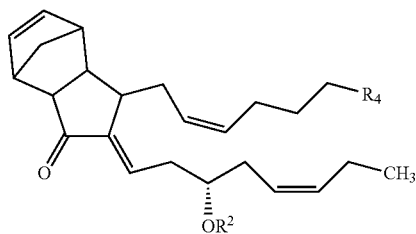
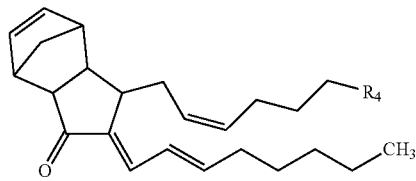
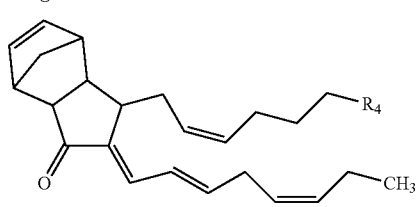
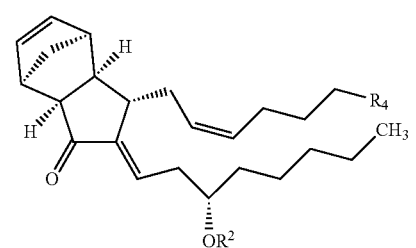
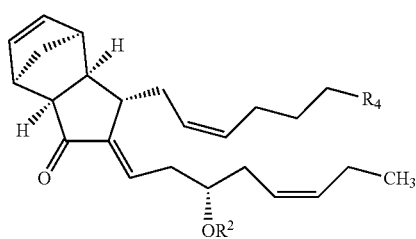
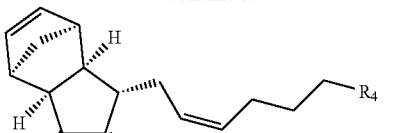
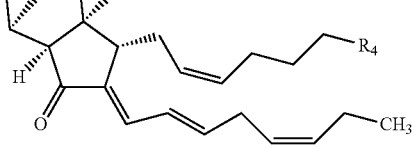
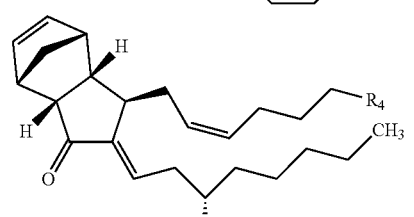
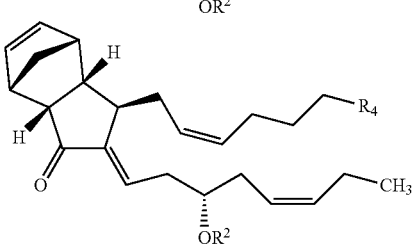
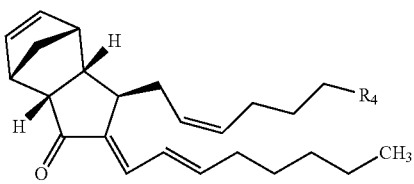
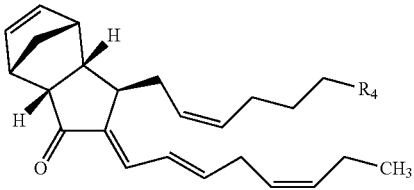
The compositions of Formula (VI), (VI-A), and (VI-B) may be represented more specifically as.
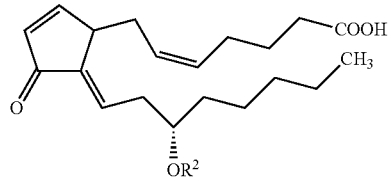
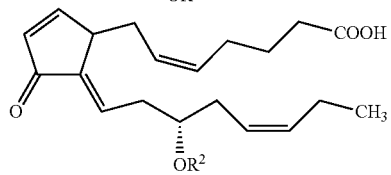

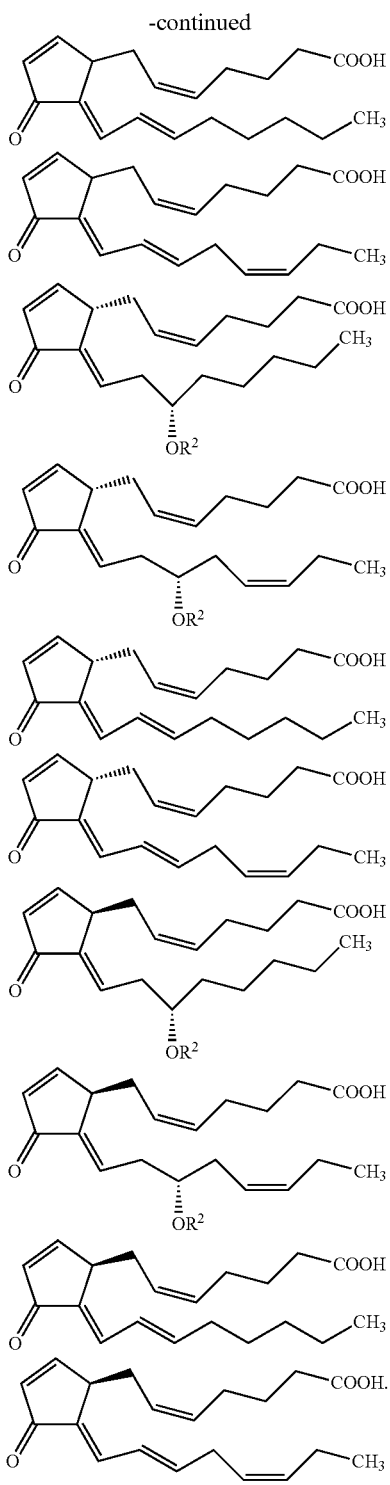

Figure 1:
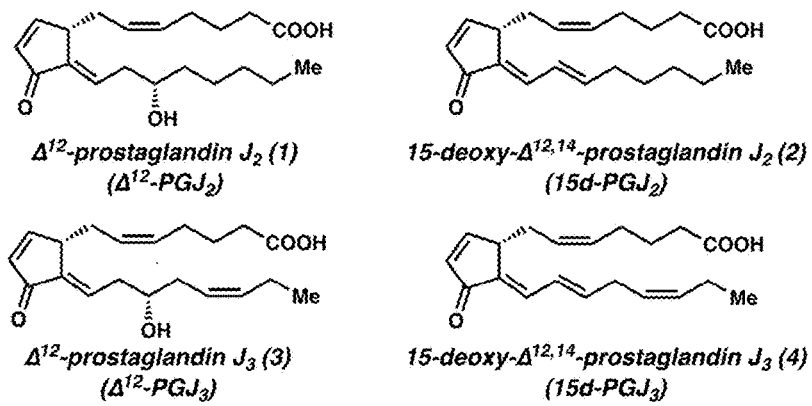
FIG. 1 shows several $\Delta^{12}$-Prostaglandin J Natural Products described in this disclosure.

These compounds of Formula (VI-B) correspond to the target prostaglandins as shown in FIG. 1.

In the context of these compositions, the olefin moieties are presented here as directed to specific cis and trans configurations. While individual molecules may comprise these configurations, mixtures of individual molecules present in compounds or compositions allow for the presence of minor amounts of the other isomer. For example, in certain embodiments, compositions (which may be referred to as compounds) include molecules in which the respective cis olefins may contain some trans content, and vice versa. In some embodiments, at least one nominally cis-configured carbon-carbon double bond has a Z/E-selectivity of 90/10 or higher. In preferred embodiments, at least one nominally cis-configured carbon-carbon double bond has a Z/E-ratio of 95/5, 96/4, 97/3, or 98/2, 99/1, or higher, essentially 100/0. In additional embodiments, each of the cis-configured carbon-carbon bonds independently has one of these Z/E ratios. Likewise, in some embodiments, the trans-configured carbon-carbon double bond in the ω-chain has an E/Z-selectivity of 90/10 or higher. In preferred embodiments, the trans-configured carbon-carbon double bond in the ω-chain has an E/Z of 95/5, 96/4, 97/3, or 98/2, 99/1, or higher, essentially 100/0. Again, in additional embodiments, each of the trans-configured carbon-carbon bonds independently has one of these E/Z ratios.

Likewise, the compounds of Formula (I-A)/(I-B), Formula (II-A)/(II-B), Formula (III-A)/(III-B), Formula (IV-A)/(IV-B), Formula (V-A)/(V-B), and Formula (VI-A)/(VI-B) are shown as single, pure enantiomers, but it should be recognized that these represent limits of enantiomeric purity. In some embodiments, these respective structures may reflect instead enantiomerically enriched compositions of Formula (I), Formula (II), Formula (III), Formula (IV), Formula (V), and Formula (VI), respectively. Within this context, each of the compositions designated Formula (I-A/B), (II-A/B), (III-A/B), (IV-A/B), (V-A/B), and) VI-A/B) may independently exhibit enantiomeric excesses of 95%, 96%, 97%, 98%, 99%, 99.5%, 99.8%, or higher. These highly enantiomerically pure intermediates can be used to generate correspondingly highly enantiomerically pure downstream derivatives, including highly enantiomerically pure prostaglandin J natural products. In some embodiments, the enanopurities of these compositions generally derive from the enantiomeric purities of the corresponding " ⟋ " and " ⟍ " orientations and the ability of the methods to make and retain the stereospecificity of these bonds. In these and other transformations, the retention of the enantiopurity are specific embodiments.

This disclosure also sets forth methods for making these intermediates, in racemic, enantioenriched, and enantiopure (>98% ee) forms. For examples, certain embodiments set forth herein include those methods of making a compound of Formula (I) (and its enriched enantiomers of nominal Formula (I-A) and (I-B)) by coupling an allyl group and an ω-chain to a compound of Formula (II),

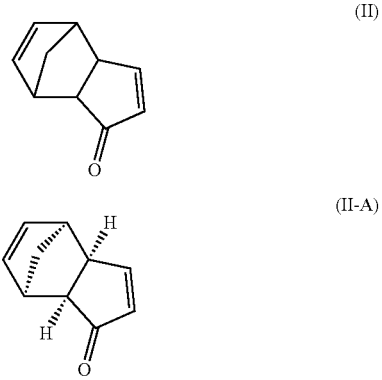

-continued

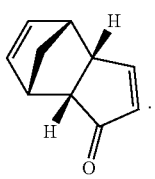
(II-B)

To access the enantio-enriched 3-oxodicyclopentadiene moiety, there are several reported methods including enzymatic resolution by lipases (Tanaka, K., et al., *Synthesis* 1995, 1995, 1237-1239) or keto reductases (Karki, K., et al., *Synlett* 2018, 29, 1723-1728.), a Cocatalyzed asymmetric intermolecular Pauson-Khand reaction (PKR) of norbornadiene and alkynes ((a) Orgué, S., et al., *Org. Lett.* 2015, 17, 250-253. (b) Verdaguer, X., et al., *J. Org. Chem.* 2004, 69, 8053-8061.), or kinetic resolution via a Cu-catalyzed 1,3-dipolar cycloaddition reaction (Chang, X., et al., *Org. Lett.* 2019, 21, 1191-1196). Each of these references cited are incorporated by reference herein for their teaching of the respective methods as applicable for use in the present reaction scheme. This disclosure exemplifies the lipase-mediated enzymatic resolution to synthesize enantiomerically pure starting materials, since racemic endo-3-oxodicyclopentadiene can be readily obtained through one-pot allylic photooxidation of dicyclopentadiene catalyzed by tetraphenylporphyrin (TPP) as a photosensitizer. The details of this exemplification is set forth elsewhere herein and when considered in the context of other reactions represent separate embodiments of this disclosure.

In preferred embodiments, the transformation of compounds of Formula (II), (II-A), and (II-B) to of compounds of Formula (I), (I-A), and (I-B) to is accomplished by selective conjugate addition of an allyl group (for example, using an organocopper allyl source) to the respective racemic or chiral 3-oxodicyclopendadiene, and trapping the resulting enolate by subsequent addition of an aldehyde of Formula (O-1), (O-2), (O-3), or (O-4), respectively:

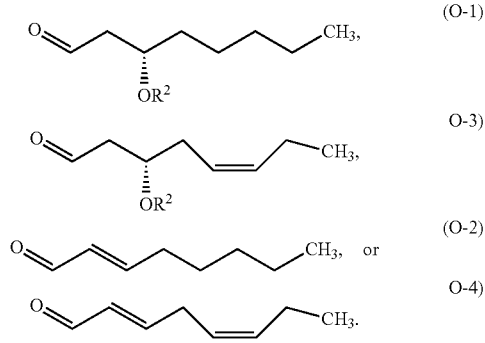

This trapping results in the formation of an aldol intermediate that can be dehydrated to form the compound of Formula (I).

In preferred embodiments, the organocopper allyl source is a bis-allyl copper reagent, for example derived from the admixture of a copper halide (e.g., CuCl, CuBr, CuI) and an allyl Grignard reagent, typically in the presence of an organic sulfide (e.g., Me$_2$S) and an alkali metal halide, especially a lithium halide such as LiCl. Such systems are also known as Gilman reagents, in which the reactive reagent is contemplated to be (allyl)$_2$CuLi, or equivalent Other sources of allyl (e.g., allyl lithium or allyl Grignard reagents) may be considered as well, but these are much less desirable for their lack of enone selectivity. The organocuprates are preferred as selective for conjugate addition with α,β enones, whereas, using the precursors of Formula (II), (II-A), or (II-B), the corresponding Grignard or allyl lithium would undesirably add to the carbonyl carbon. The stereochemistry of the conjugate addition by the Gilman reagents is controlled by steric factors providing the desired stereochemistry in the present scheme in high stereochemical yield.

The product of the 3-component coupling reaction results in the formation of a diastereomeric aldol intermediate which may or need not be isolated. In the case where the compound of Formula (II-A) is subjected to the reaction conditions with 0-2 as the trapping aldehyde, the intermediate S-1 was identified as the major aldol diastereomer (see Examples), indicating that the mechanism proceeds through an anti-aldol process

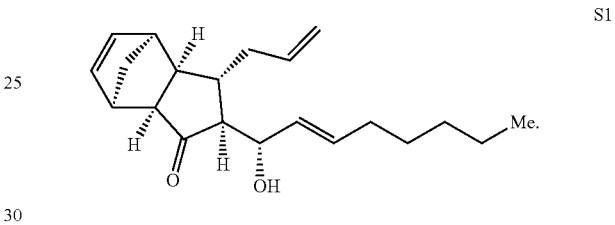
S1

It is believed that analogous intermediates are generated in the other-mentioned reactions Dehydration of these aldol intermediates results in the formation of compounds having a structure of Formulae (I), (I-A), or (I-B), respectively In certain embodiments, this transformation is accomplished by reacting the aldol intermediate with a sulfonylating agent and a base to form the desired product compound with complete retention of the enantiomeric purity. In certain preferred embodiments, these sulfonylating agents include optionally (per)fluorinated alkylsulfonyl chloride or an optionally substituted arylsulfonyl chloride, such as optionally substituted MsCl, TfCl, TsCl. Use of these reagents conveniently convert the aldol alcohol into a good leaving group for elimination with base. Preferred bases include non-nucleophilic bases, including hindered nitrogen bases, such as dimethylaminopyridine, 2,6-lutidine, 2,6-di-tert-butyl-4-methylpyridine (DTBMP), and diisopropylamine. These reagents together result in the effective elimination of water from the aldol intermediate to form the thermodynamically favored trans-exocyclic 2-alkylidene moiety.

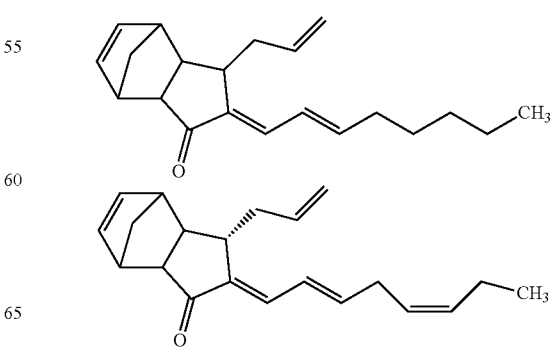

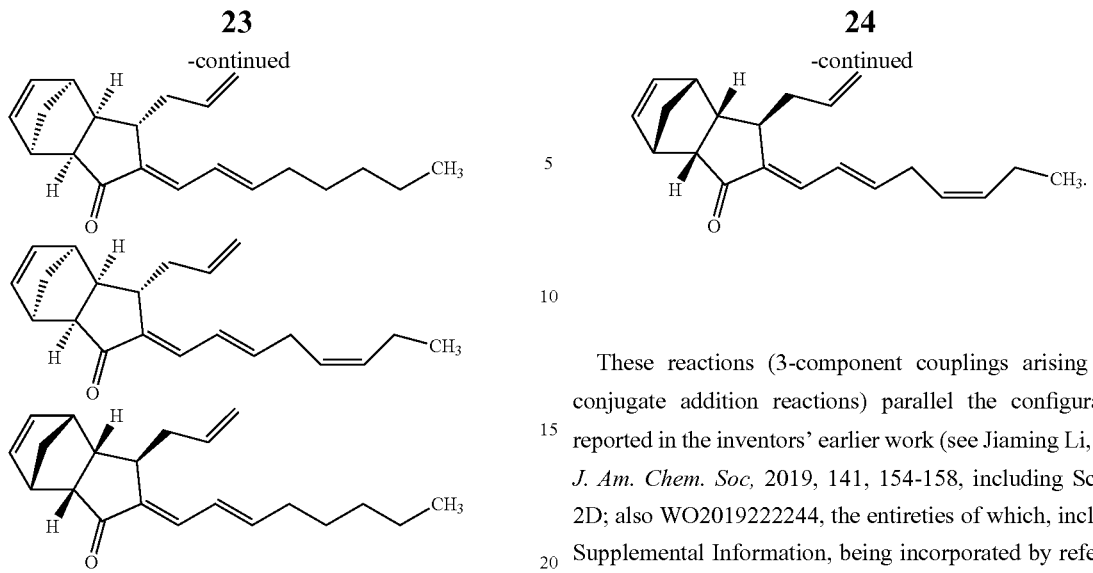

Figure 4:
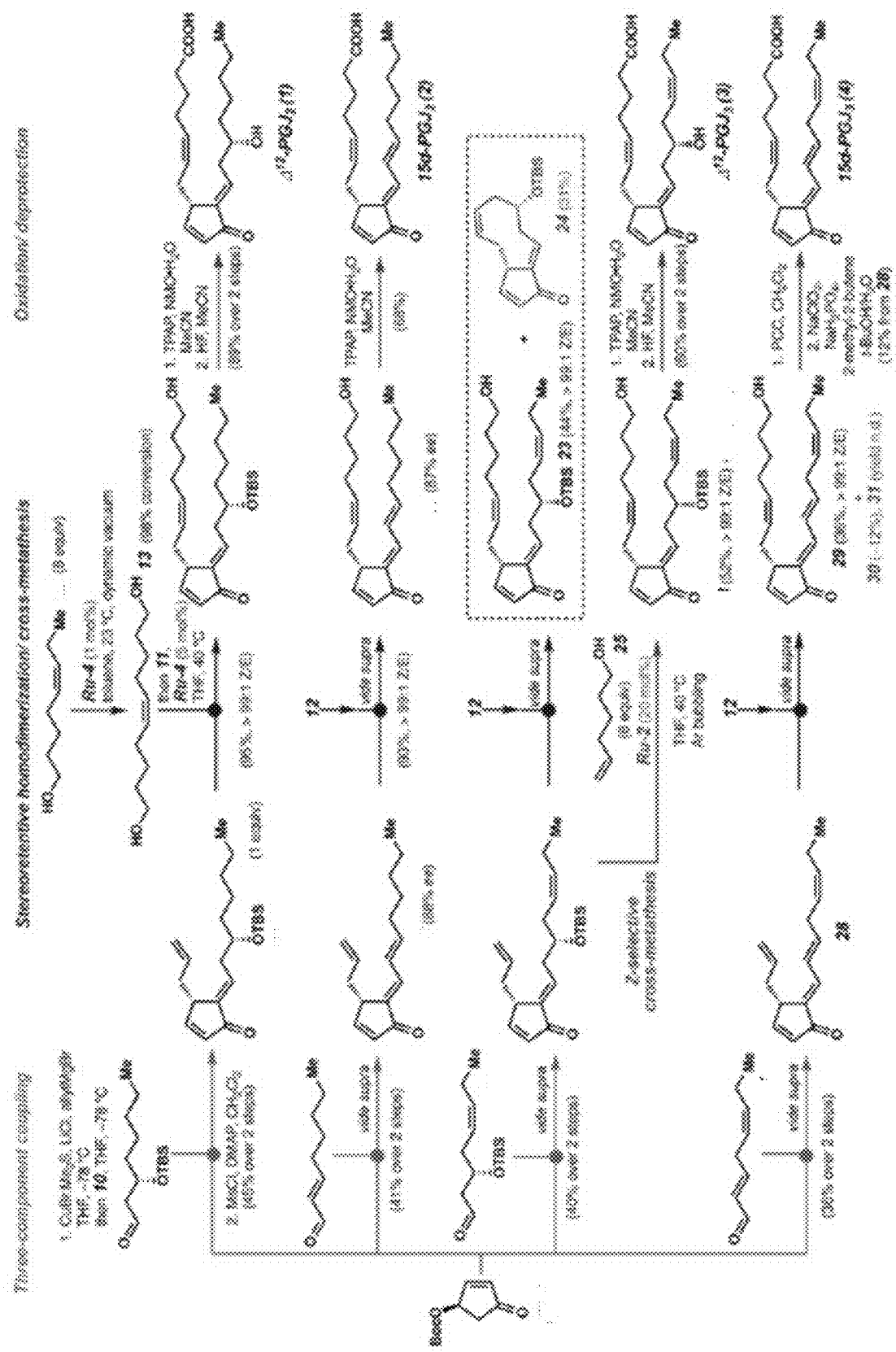
FIG. 4 shows synthetic scheme for fuller range of prostaglandin $J_2$ natural products as set forth in Jiaming Li, et al., J. Am. Chem. Soc, 2019, 141, 154-158.

These reactions (3-component couplings arising from conjugate addition reactions) parallel the configurations reported in the inventors' earlier work (see Jiaming Li, et al., *J. Am. Chem. Soc,* 2019, 141, 154-158, including Scheme 2D; also WO2019222244, the entireties of which, including Supplemental Information, being incorporated by reference here their entireties)(see also FIG. 4),

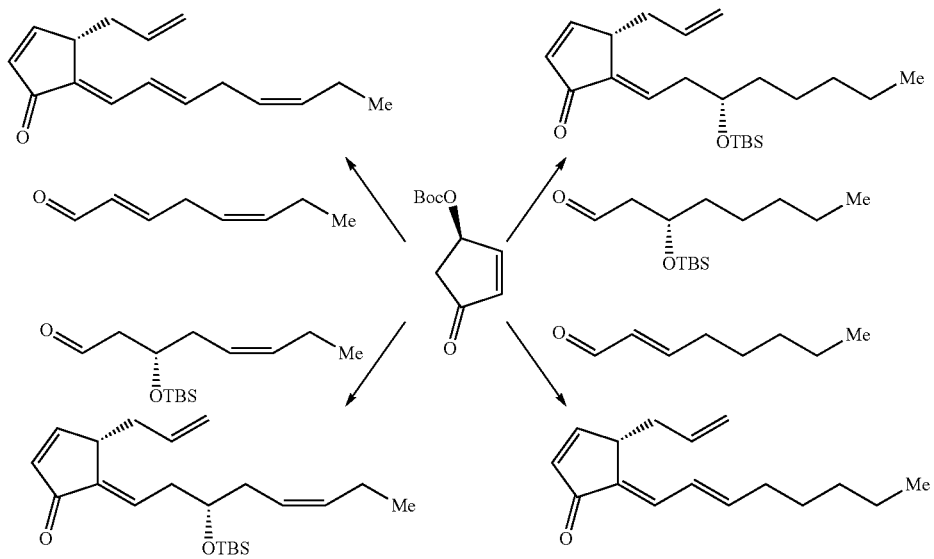

In independent embodiments, the compounds of Formula (I), or their enriched enantiomers Formula (IA) or (I-B) serve as useful precursors for the downstream reactions to form prostaglandin J natural products (or their protected derivatives) by steps which include the stereoretentive formation of the cyclopentenone ring structure and Z-selective or stereoretentive metathesis of the allyl group to form a Z-enriched olefin as is characteristic of these prostaglandin materials. These steps (retro-Diels Alder and Z-selective/stereoretentive metathesis) can be independently applied in either order. For example,

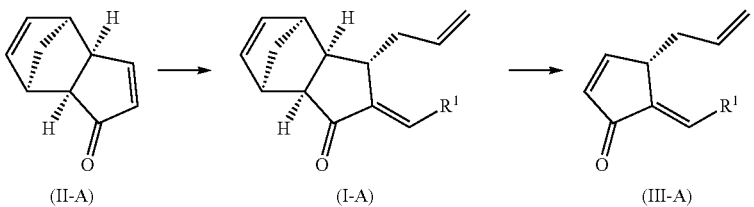

-continued

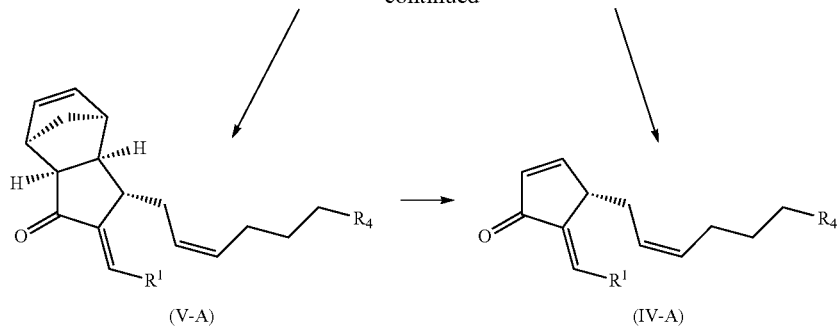

(V-A)          (IV-A)

For example, certain embodiments provide for the conversion of compounds of Formula (I), (I-A), and/or (I-B) to compounds of Formula (III), (III-A), and/or (III-B), respectively:

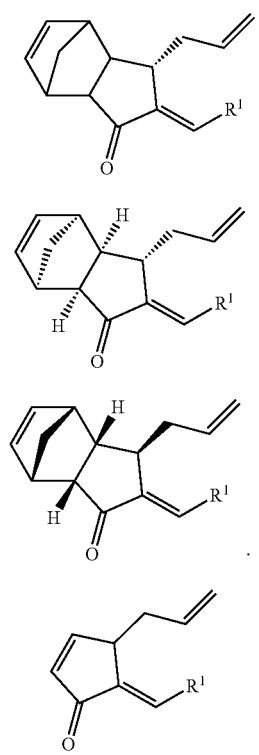

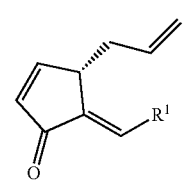

(III-A)

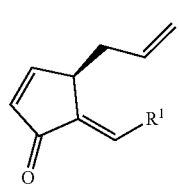

(III-B)

by subjecting the compounds of Formula (I), (I-A), and/or (I-B) to conditions suitable for effecting a retro-Diels Alder reaction to form the compounds of Formula (III), (III-A), and/or (III-B), respectively. Preferably, these retro-Diels Alder reaction conditions include the use of Lewis acid catalysts, such as use of zinc chloride, boron trifluoride, tin tetrachloride, aluminum chloride, or organometallic derivative thereof. In preferred embodiments, the Lewis acid catalyst is an organoaluminum chloride, such as methyl or ethyl aluminum chloride(s), in the optional presence of an olefin (e.g., maleic anhydride). The use of these Lewis acid catalysts allows for the use of lower reaction temperatures otherwise associated with retro-Diels Alder reaction. Such reactions are similar to those developed by Grieco, P. A., et al., *J. Org. Chem.* 1989, 54, 6008-6010, which is incorporated by reference herein at least for its teaching of these methods. The use of Lewis acid catalysts is known to be useful in mitigating the otherwise aggressive temperature conditions associated with retro-Diels Alder reactions (see Nicolaou, K. C., et al., *J. Org. Chem.* 2019, 84, 365-378, which are all incorporated by reference herein for their teaching of alternative retro-Diels Alder conditions) and allowing for the desired conversions at temperatures of less than 100° C. or less than 90° C. or about 80° C. Using these catalysts and associated reaction conditions, the excellent enantiopurities now available in the compounds of Formula (I-A) or (I-B) can be retained in the product compounds of Formula (III-A) or (III-B), respectively.

Certain embodiments of the present disclosure also provide for the conversion of compounds of Formula (III), (III-A), and/or (III-B) to compounds of Formula (IV), (IV-A), and/or (IV-B), respectively:

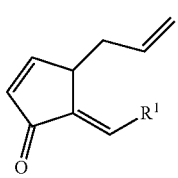

(III)

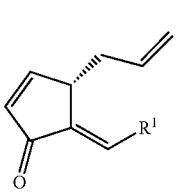

(III-A)

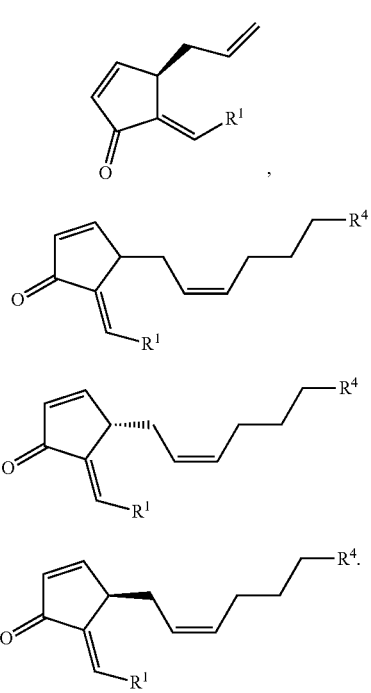

by reacting the compounds of Formula (III), (III-A), and/or (III-B) with a compound of Formula (ZO-1) or preferably (ZO-2), in the presence of a Z-selective or stereoretentive olefin metathesis catalyst:

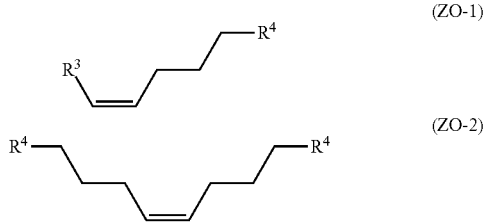

where $R^3$ is H or a $C_{1-3}$alkyl, preferably a C1 or C2 alkyl;
$R^4$ is independently $CH_2$—$OR^2$, an optionally protected carboxylate (—COOH), optionally protected aldehyde (—CHO), or a cyano (—CN);
to form the compound of Formula (IV), (IV-A) or (IV-B), respectively.

As shown elsewhere herein, the use of the ZO-2 olefins are preferred to minimize unwanted side reactions resulting from the competitive coupling of the R3 containing olefin subunit with the allyl group of the compounds of Formula (III), (IIIA), or (III-B). These can used directly or generated in situ by the reaction cross-coupling of the olefin of (ZO-1). While the ZO-1 olefins can also be used directly as starting materials, as shown elsewhere herein these are preferably metathesized in the presence of a suitable Z-selective or stereoretentive olefin metathesis catalyst, preferably under high vacuum, before contacting with the compounds of Formula (III), (IIIA), or (III-B). The conditions of the prior metathesis are such that the more volatile $R^3$—CH═CH—$R^3$ coproducts are preferentially removed. While $R^3$ is set forth herein as H or $C_{1-3}$alkyl, other options for $R^3$ can be used, provided the olefin coproduct is preferentially removed during the metathesis.

Also, note that the nature of $R^3$ (i.e., H or alkyl capped) may define the choice of the metathesis catalyst, as is known in the art.

Also, in its most general sense, $R^4$ can be any substituent capable of later conversion to the targeted carboxylic acid group. The options presented here represent convenient options for this purpose. As shown herein, $R^4$ is —$CH_2OH$ is suitable for this purpose, and being the simplest option, is preferred. However, groups such as the corresponding protected alcohols, optionally protected carboxylato (—COOH), optionally protected aldehyde (—CHO), and a cyano (—CN) are also suitable alternatives. Alcohol, aldehyde, and carboxylic acid protective groups are well known, as are the methods for adding and removing them. Again, see Greene & Wuts, Protective Groups in Organic Synthesis, 3rd Ed., John Wiley & Sons, New 5 York, N Y, 1999, and Kocienski, Protective Groups, Thieme Verlag, New York, N.Y., 1994, the contents of each of which are incorporated herein by reference at least these disclosures. In the case where the Z-selective or stereoretentive olefin metathesis catalyst tolerates the alcohol, aldehyde, or carboxylic acid end groups, as has been shown to be the case for many of these metathesis catalysts, their protection is not required.

In preferred embodiments, the Z-selective or stereoretentive olefin metathesis catalyst (and the associated metathesis reaction conditions) with the allyl moiety and the ZO-1 or ZO-2 olefins to provide for the formation of the cis-olefin with a Z/E selectivity of at least 90/10, and in most preferred embodiment of at least 95/5, at least 96/4, at least 97/3, at least 98/2, at least 99/1, at least 99.5/0.5, or practically 100/0.

In some embodiments, the Z-selective or stereoretentive olefin metathesis catalyst is a Z-selective or stereoretentive olefin metathesis catalyst based on Group 8 metals (e.g., Ru and Os), preferably based on ruthenium. These catalysts may also be characterized as Z-selective or stereoretentive Grubbs or Grubbs/Hoveyda olefin metathesis catalysts. Some such catalysts are described in the following references, each of which is incorporated by references herein, at least for their teachings of these catalysts and the conditions of their use: (a) Rosebugh, L. E. et al., *J. Am. Chem. Soc.*, 2013, 135, 1276-1279; (b) Montgomery, T. P., et al., *Angew. Chem., Int. Ed.* 2017, 56, 11024-11036. (c) Ahmed, T. S, et al., *Angew. Chem., Int. Ed.* 2017, 56, 11213-11216. (d) Ahmed, T. S., et al., *Chem. Sci.* 2018, 9, 3580-3583. (e) Jung, K., et al., *Macromolecules* 2018, 51, 4564-4571; Keitz, B. K., et al., *Am. Chem. Soc.* 2011, 133, 9686; Keitz, B. K., et al., *J. Am. Chem. Soc.* 2012, 134, 693; Keitz, B. K., et al., *J. Am. Chem. Soc.* 2012, 134, 2040; Endo, K., et al., *J. Am. Chem. Soc.* 2011, 133, 8525. Also, such catalysts are described in U.S. Pat. Nos. 10,265,691; 9,938,253; 9,920,086; 9,795,953; 9,676,676; 9,586,981; 9,457,347; 9,303,100; 8,716,488; 8,039,566; and 7,094,898; and U.S. Patent Application Publ. No. 20200102285, all of which are incorporated by reference herein for their teachings of these catalysts and the conditions of their use. Representative catalysts include, but are not limited to, those exemplified in this work:

Z-selective metathesis catalysts:

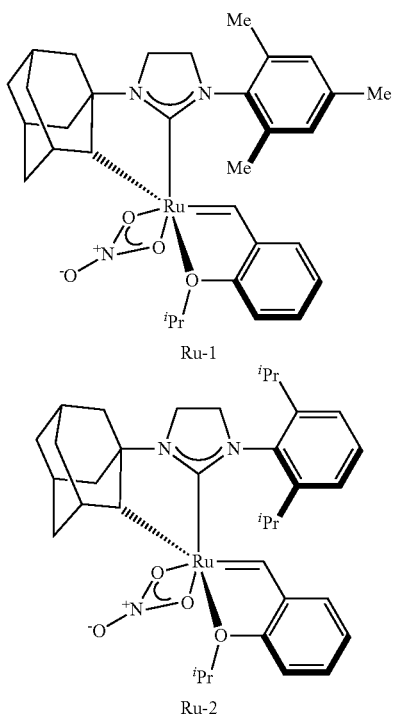

Ru-1

Ru-2

Stereoretentive metathesis catalysts:

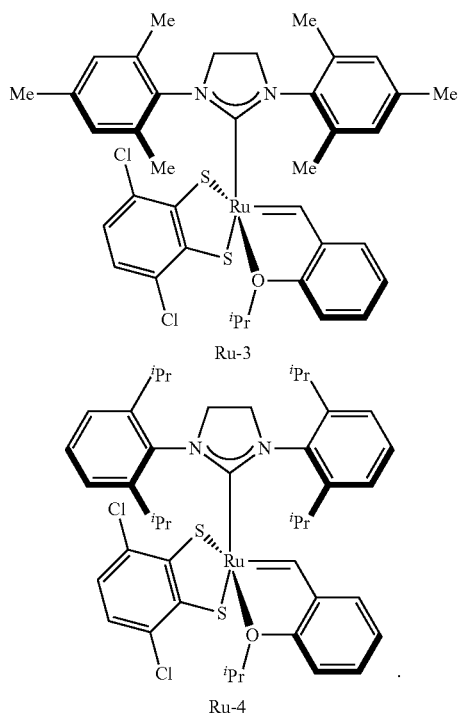

Ru-3

Ru-4

Figure 5A:
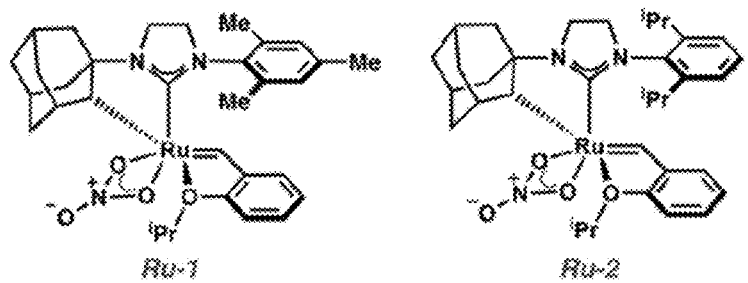
FIGS. 5A-C shows illustrative Z-selective/stereoretentive Ruthenium catalysts useful in the presented methods.
Figure 5A:
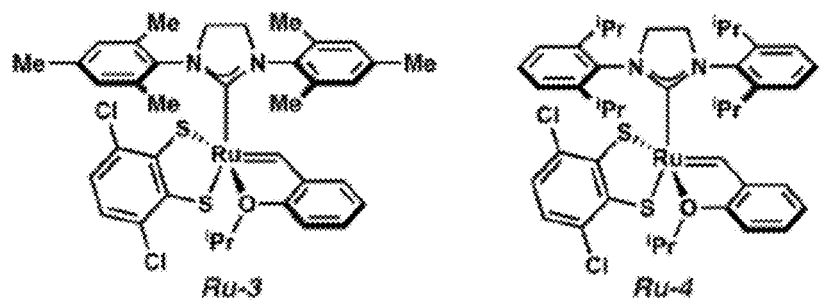
Figure 5B:
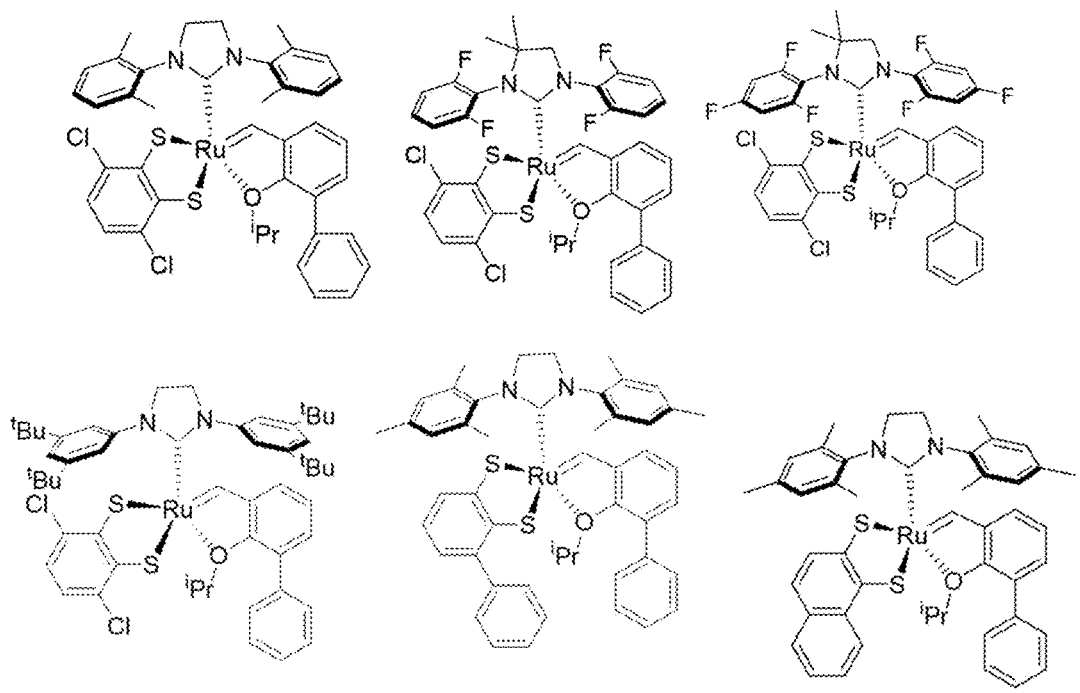
Figure 5C:
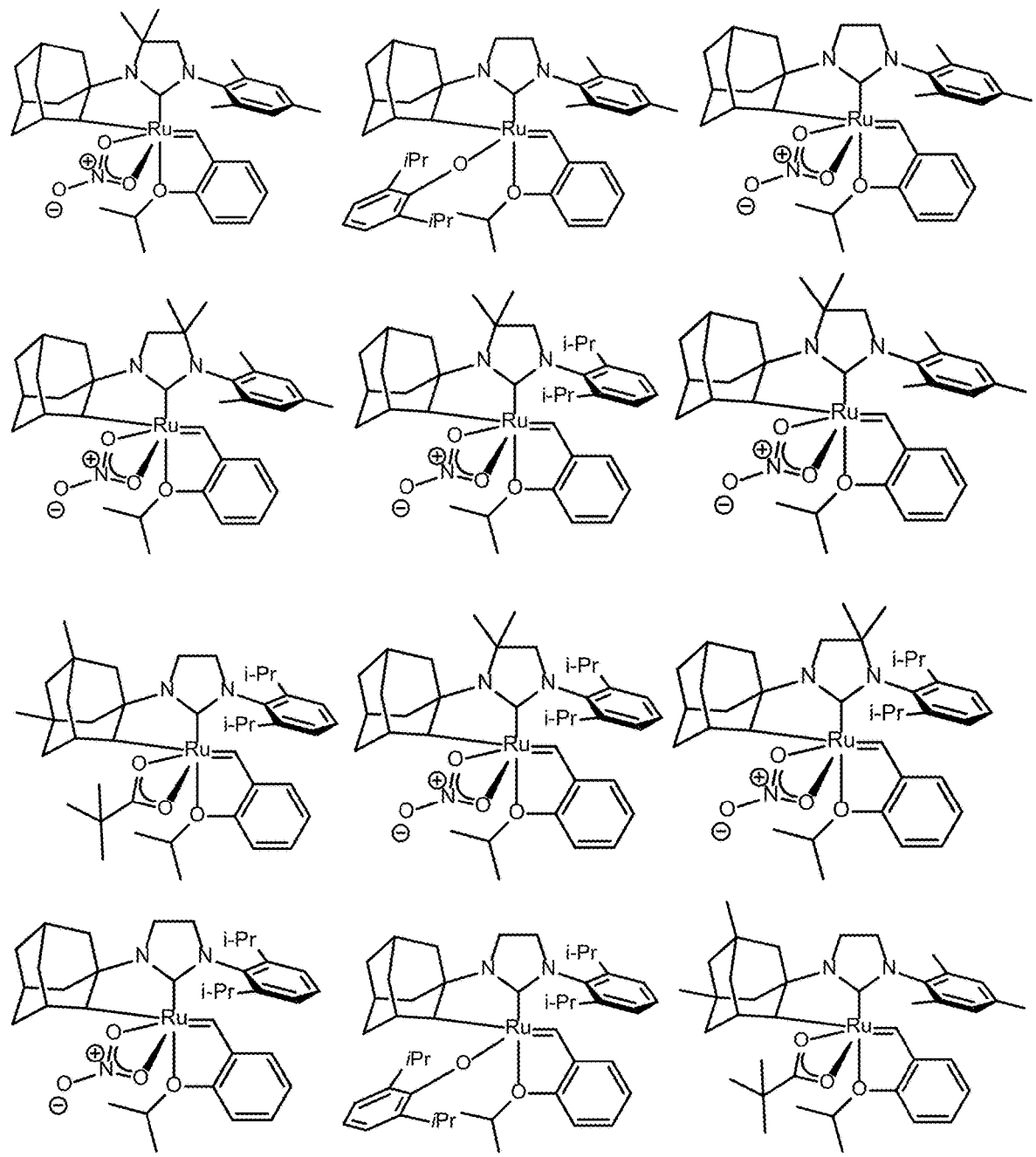

See also FIGS. 5A-C.

Figure 6:
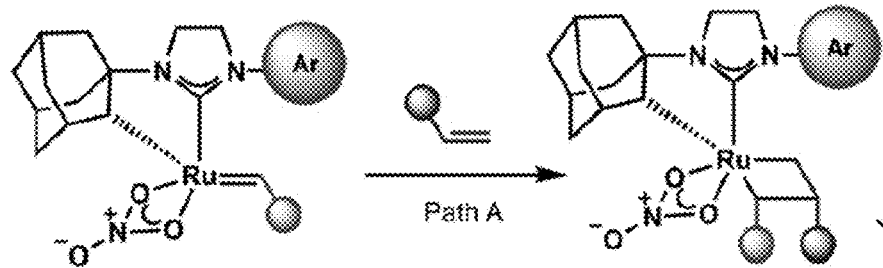
FIG. 6 shows models of stereoselectivity for Z-selective and stereoretentive metathesis catalysts.
Figure 6:
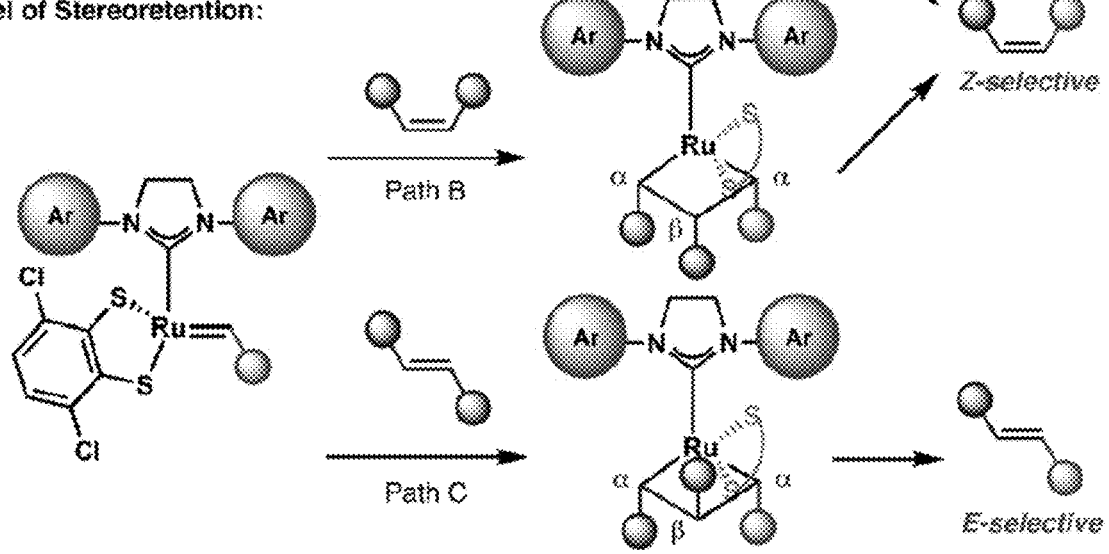

The relevant utilities of these different types of catalysts is well understood. A series of cyclometalated ruthenium-based catalysts (e.g., Ru-1, Ru-2, above) is described at least in (a) Endo, K., et al., *J. Am. Chem. Soc.* 2011, 133, 8525-8527; (b) Keitz, B. K.; Endo, K, et al., *J. Am. Chem. Soc.* 2012, 134, 693-699; (a)) that enabled Z-selective metathesis through a favored syn-metallacyclobutane intermediate (FIG. 6, Path A). More recently, catechodithiolate-based catalyst Ru-3 and its dithiolate variants were developed that showed high Z-selectivity in ring-opening metathesis polymerizations, ring-opening cross-metathesis, and cross-metathesis with Z-olefins. See. e.g., (a) Khan, R. K. M., et al., *J. Am. Chem. Soc.* 2013, 135, 10258-10261. (b) Hoveyda, A. H., *J. Org. Chem.* 2014, 79, 4763-4792. (c) Koh, M. J, et al., *Angew. Chem., Int. Ed.* 2014, 53, 1968-1972. (d) Koh, M. J., et al., *Nature* 2015, 517, 181-186.) In fact, high kinetic E-selectivity in cross metathesis with E-starting materials was also observed with Ru-3, the sTPr analogue Ru-4, and other less bulky fast-initiating analogues developed, that defined these catalysts as stereoretentive; see, e.g., (a) Johns, A. M., et al., *Org. Lett.* 2016, 18, 772-775. (b) Ahmed, T. S., et al., *J. Am. Chem. Soc.* 2017, 139, 1532-1537. The origin of the stereoretention was attributed to the formation of a side-bound metallacyclobutane intermediate, of which the α-substituents are forced down to minimize steric interactions with the bulky N-aryl groups of the NHC. As a result, when starting with Z-alkenes, the β-substituent points down to generate Z-alkene products (FIG. 6, Path B, see also Li, J, et al., *J. Am. Chem. Soc.*, 2019, 141, 154-158, which is incorporated by reference herein in its entirety). When starting with E-alkenes, however, the β-substituent has to point up into the open space between two N-aryl groups, leading to the generation of E-alkene products, albeit with slower rates (FIG. 6, Path C). Cross-metathesis between two terminal alkenes is not possible with stereoretentive metathesis catalysts, however, because the intermediate methylidene species are unstable and lead to catalyst decomposition. (Koh, M. J., et al., *Nature* 2015, 517, 181-186). A methylene capping strategy was recently reported as a remedy to this problem, enabling the cross-metathesis of two terminal alkenes. See, e.g., Xu, C., et al., *J. Am. Chem. Soc.* 2017, 139, 10919-10928.

In some other embodiments, the Z-selective olefin metathesis catalyst is a Z-selective or stereoretentive olefin metathesis catalyst based on Group 6 metals (e.g., Cr, Mo, and W), preferably based on Mo or W. These catalysts may also be characterized as Z-selective or stereoretentive Schrock-type olefin metathesis catalyst, including monoalkoxide pyrrolide (MAP) tungsten (W) and molybdenum (Mo) catalysts. Such catalysts are described in the following references, each of which is incorporated by references herein, at least for their teachings of these catalysts and the conditions of their use: Stereoretentive metathesis using Mo, W: (a) Couturier, J.-L., et al., *Int. Ed. Engl.* 1992, 31, 628-631. (b) Lam, J. K., et al., *J. Am. Chem. Soc.* 2016, 138, 15774-15783. (c) Nguyen, T. T., et al., *Science* 2016, 352, 569-575; (d) Shen, X., et al., *Nature* 2017, 541, 380-385. (e) Koh, M. J., et al., *Nature* 2017, 542, 80-85. Also, such stereoretentive and Z-selective catalysts are described in U.S. Pat. Nos. 10,343,153; 0,173,208; 10,106,566; 10,072, 036; 9,919,299; 9,850,268; 9,771,386; 9,713,808; 9,701, 702; 9,446,394; 9,441,059; 9,409,938; 9,315,604; 9,206, 211; 9,085,595; 9,079,173; 9,073,801; 8,598,400; 8,546, 500; 8,362,311; 7,652,145; 7,378,528; 7,294,717; 6,787, 620; 6,635,768; and 6,552,139, all of which are incorporated by reference herein for their teachings of these catalysts and the conditions of their use.

In some embodiments, the compounds of Formula (I), (I-A), and/or (I-B) are subjected to Z-selective or stereoretentive olefin metathesis conditions as set forth above to form the compounds of Formula (V), (V-A), and/or (V-B), before being subjecting to the retro-Diels Alder reaction conditions also set forth above to form the compounds of Formula (IV), (IV-A), and/or (IV-B) under the same or similar conditions described for each of these respective steps.

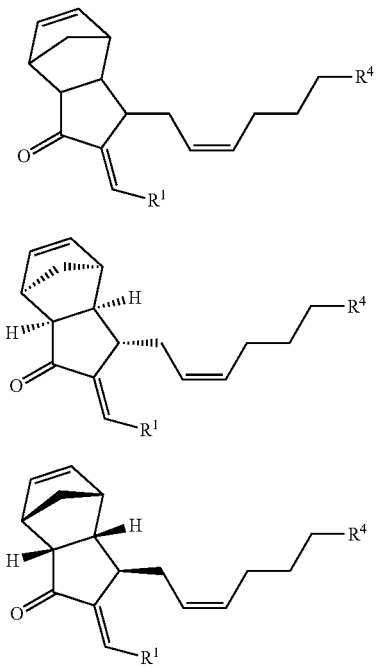

Once prepared, the compounds of Formula (IV), (IV-A), and/or (IV-B) can be converted to their corresponding prostaglandin J natural products of Formula (VI), (VI-A), and/or (VI-B), or derivatives thereof, by known methods.

For example, procedures for the removal of the respective protecting groups from any alcohol, aldehyde, or carboxylic acid are known, as set forth above.

The conversion of cyano groups to carboxylic acid groups by acid or base catalyzed hydration are also known.

The oxidation of primary alcohols (—CH$_2$OH=>—COOH) known to be catalyzed directly by oxidizing reagents including KMnO$_4$, Jones oxidation reagent (CrO$_3$ and sulfuric acid), or PDC (pyridinium dichromate) in DMF, or by stepwise oxidation of the alcohol to the aldehyde (e.g., by e.g. iodobenzoic acid (IBX) oxidation, Dess-Martin periodinane, or TEMPO/NaOCl) and then the carboxylic acid (e.g., by Pinnick oxidation using sodium chlorite). Some of these reagents are extremely aggressive (KMnO$_4$) or hazardous (CrO$_3$ and sulfuric acid) and the milder reagents are preferred if only to avoid these issues. Preferred methods are discussed elsewhere herein.

Exemplary Description of Synthesis of Enantiopure 15d-PGJ$_2$

While comments made in this section are specifically directed to the use of compounds of Formulae (I-A) to (IV-A) where R$^1$ is P$_2$, it should be appreciated that such methods/teachings are applicable also to the other compositions set forth elsewhere herein. Also, the reader is referred to FIGS. 7-10 for the number designations of the specific compounds set forth in this section.

Figure 7A:
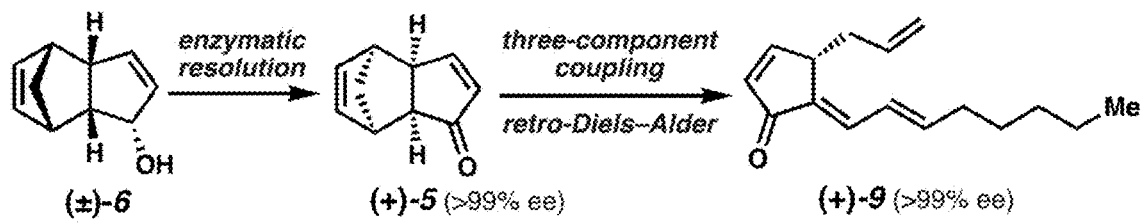
FIG. 7A shows improved route enabled by a three-component coupling/retro-Diels Alder strategy, this work.

The following represents an exemplary process for the preparation of enantiopure 15d-PGJ$_2$. It is not intended to supersede the more general teachings, but it is useful for illustrating the nature of some of the transformations set forth herein. To the extent that As shown in FIGS. 7A/B, starting from enantiopure 3-oxodicyclopentadiene ((+)-5, the intermediate (+)-9 can be obtained in high enantioselectivity (FIGS. 7A/B, 8, >99% ee), providing access to enantiopure 15d-PGJ$_2$ and other prostaglandin J intermediates The steps, methods, and intermediates set forth in the following descriptions are representative of the more general concepts described elsewhere herein. The following then provides additional non-limiting embodiments of the foregoing descriptions.

Of the several methods of preparing the enantio-enriched 3-oxodicyclopentadiene moiety, this disclosure exemplifies a lipase-mediated enzymatic resolution of racemic endo-3-oxodicyclopentadiene (±)-5 to synthesize enantiomerically pure 5. Upon reduction of the racemic form with DIBAL-H, the endo-alcohol (±)-6 was obtained in excellent yield. Kinetic resolution was successfully performed on 4.0 g scale when (±)-6 was treated with vinyl acetate (0.6 equiv) in tert-butyl methyl ether in the presence of commercially available lipase PS-on-Celite (10% w/w of the substrate). endo-Acetate (−)-7 (48% yield) was separated from endo-alcohol (+)-6 (49% yield) after 48 h at 37° C. Treating (−)-7 with 1 equiv of K2CO3 in methanol liberated the endo-alcohol (−)-6. Both enantiopure (+)- and (−)-5 were obtained (>99% ee, FIG. 8) by oxidation of the endo-alcohol enantiomers by TPAP and NMO, in the presence of 4 Å molecular sieves in CH$_2$Cl$_2$/MeCN. (see Mehta, G., et al., Tetrahedron Lett. 1999, 40, 991-994). Alternatively, (+)-6 can also be oxidized using conditions reported by in Hoover, J. M., et al., J. Am. Chem. Soc. 2011, 133, 16901-16910, resulting in (−)-5 in higher yield (97% yield, FIG. 8).

Figure 2:
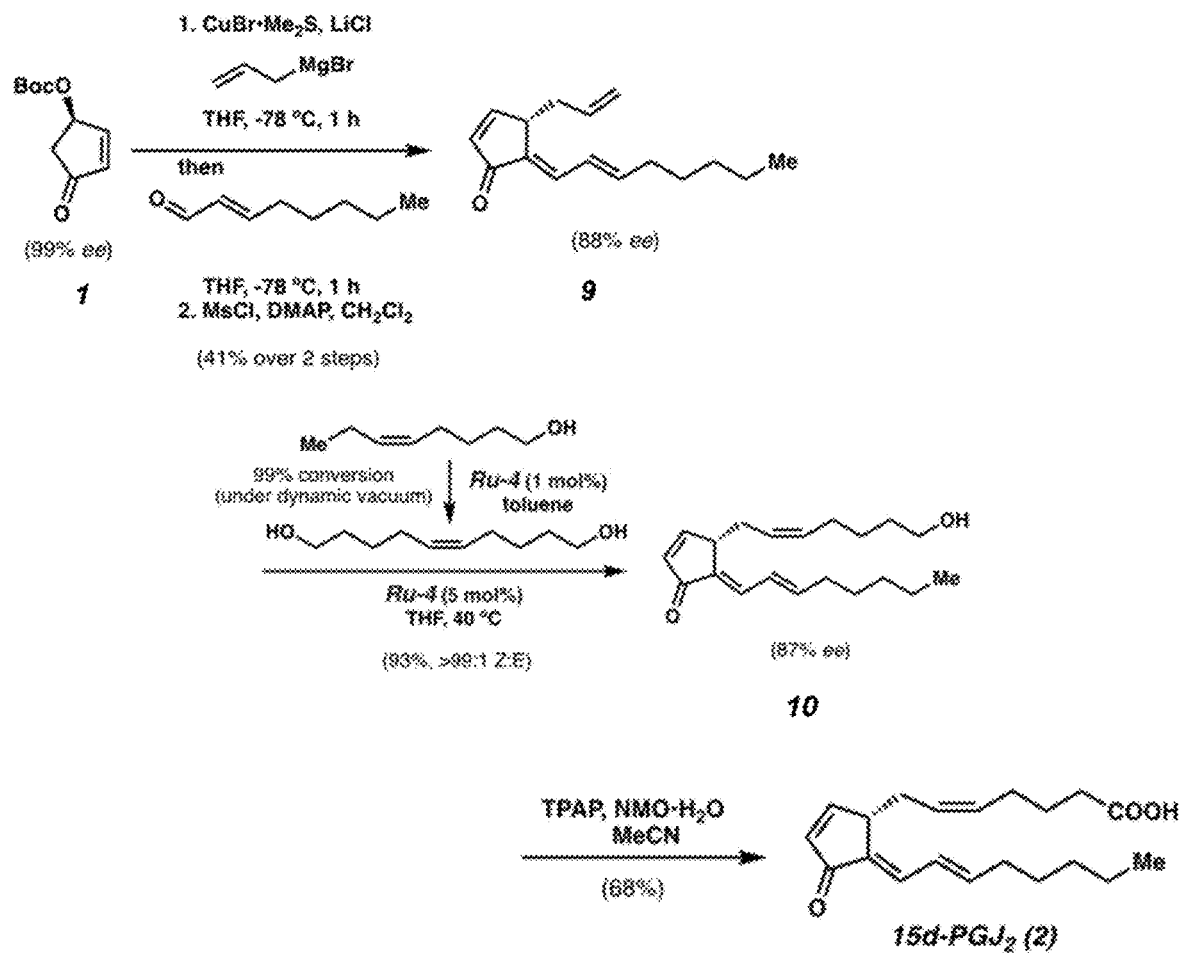
FIG. 2 shows synthetic scheme for 15d-$PGJ_2$ as set forth in Jiaming Li, et al., J. Am. Chem. Soc, 2019, 141, 154-158.
Figure 3:
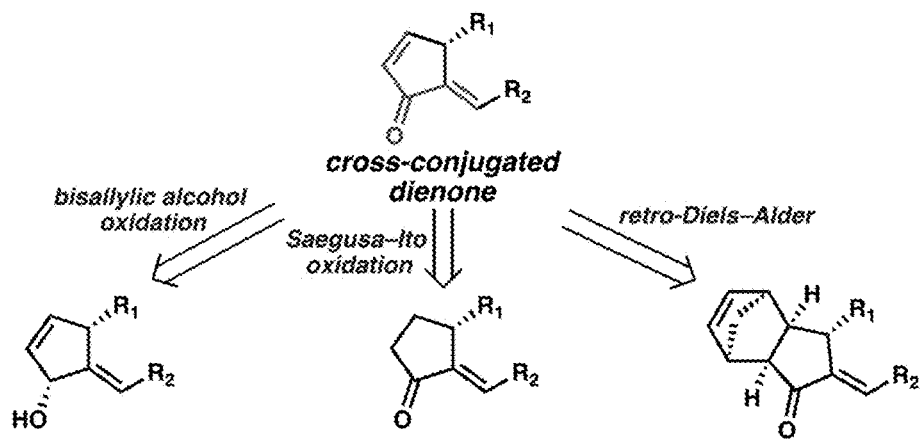
FIG. 3 shows strategies to construct cross-conjugated dienone structures.
Figure 7B:
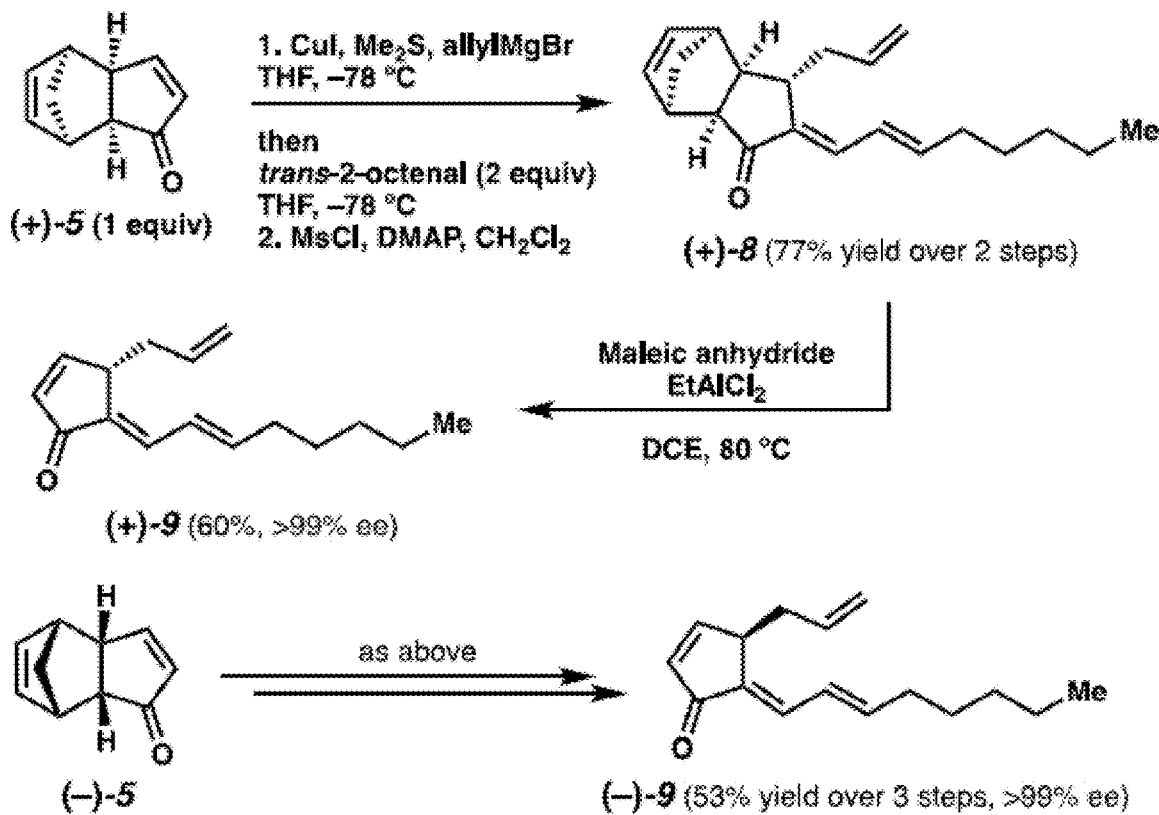
FIG. 7B shows stereodivergent synthesis of (+)- and (−)-9.
Figure 8:
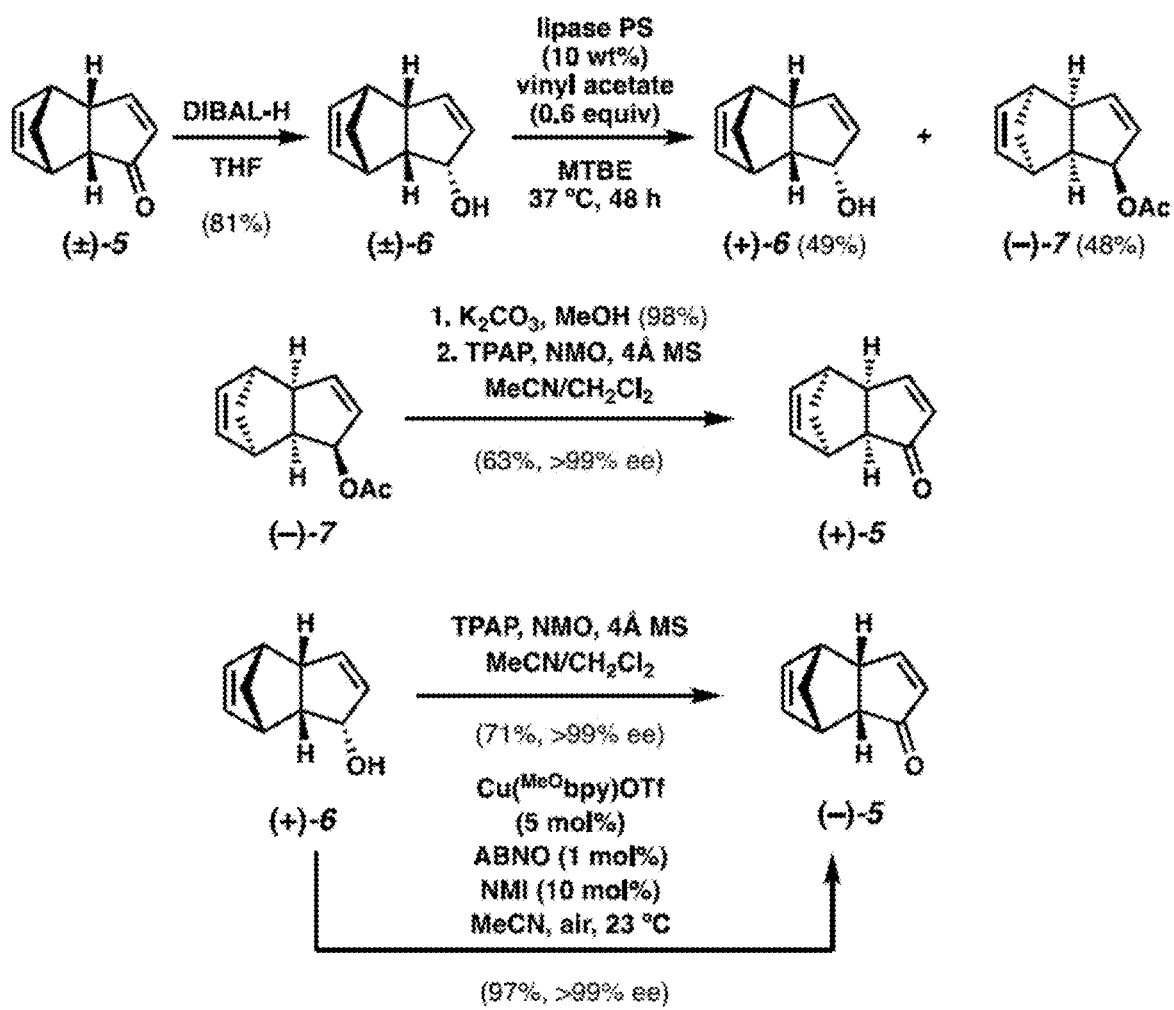
FIG. 8 shows scheme for enzymatic resolution of (±)-5 7458-7460), or bisallylic alcohol oxidation (for example, see Brummond, K. M., et al., *Org. Lett.* 2004, 6, 149-152.

Then (+)- and (−)-5 were subjected to tandem conjugate addition/aldol conditions (FIG. 9). A regio- and stereoselective conjugate addition by diallyl cuprate installed the allyl group and formed an enolate intermediate that was trapped by subsequent addition of trans-2-octenal. After elimination with MsCl and excess DMAP, the resulting mixture of aldol diastereomers, S1 vida infra) can be converted to the thermodynamically favored E-alkenes in good yield. Both enantiomers of 9 were readily obtained in high enantioselectivity (>99% ee, FIG. 9), by a Lewis acid catalyzed retro-Diels-Alder reaction developed by Grieco, using EtAlCl$_2$ and a stoichiometric amount of maleic anhydride at a lower temperature (80° C.) than the thermally induced conditions (>160° C.). In the synthesis described in Jiaming Li, et al., J. Am. Chem. Soc, 2019, 141, 154-158 ("the Li synthesis"), the preparation of (+)-9 suffered from racemization due to the acidity of the enone γ-position. The masked enone allowed us to access (+)-9 with excellent enantioselectivity. The reaction sequences reported herein are performed on a larger scale (1.6 g starting material), and the overall yields of the three-component coupling step are greatly improved compared to the Li synthesis. In addition, the enantio-enriched enone (+)-5 was used as the limiting reagent (FIG. 7B). This feature is an important improvement and an additional embodiment of this disclosure By contrast, excess (R)-12 was required (FIG. 2) in the Li synthesis report of three-component coupling reactions, presumably because the OBoc group was labile under the reaction conditions and the reaction scale was limited.

Stereoretentive olefin metathesis was critical to the success of the Li synthesis of 15d-PGJ2 in which high Z-selectivity was achieved using Ru-1. In this synthesis, (+)-9 with excess Z-alcohol 13 in the presence of 5 mol % Ru-1 under static vacuum in order to remove any volatile byproducts (1-butene, cis-3-hexene) and to favor the formation of 10. Under these conditions, the major product obtained was 11 from the reaction with propylidene (53% yield, FIG. 9), which was difficult to convert into the desired product 10 by a second cross-metathesis with alcohol 13. So, high vacuum was found to be necessary to effectively remove cis-3-hexene (bp 66-68° C.) from the reaction mixture. A one-pot homodimerization/stereoretentive metathesis method proved to be a more feasible approach, and formation of 11 could be avoided when the homodimerization step gave full conversion to afford symmetrical diol 14. The primary alcohol product 10 was obtained in 99% yield and >99% ee with high Z-selectivity (>99:1 Z/E, FIG. 9) by this procedure.

Finally, oxidation of 10 with PCC followed by Pinnick oxidation provided enantiopure 15d-PGJ2 (2) (41.0 mg, 65% yield over two steps). The enantiopurity of 2 was confirmed by synthesis of the methyl ester derivative 15 using (trimethylsilyl) diazomethane, which was obtained in 72% yield and >99% ee (FIG. 10).

Terms

The present disclosure may be understood more readily by reference to the following description taken in connection with the accompanying Figures and Examples, all of which form a part of this disclosure. It is to be understood that this disclosure is not limited to the specific products, methods, conditions or parameters described or shown herein, and that the terminology used herein is for the purpose of describing particular embodiments by way of example only and is not intended to be limiting of any claimed disclosure. Similarly, unless specifically otherwise stated, any description as to a possible mechanism or mode of action or reason for improvement is meant to be illustrative only, and while believed to be true at the time of writing, any invention disclosed herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the disclosure that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements or use of a "negative' limitation. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (or the systems used in such methods), under conditions or reagents comparable to those recited.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. Unless defined otherwise, all technical and scientific terms used herein have the same meaning as commonly understood by one of ordinary skill in the art to which any invention disclosed herein belongs. Although any methods and materials similar or equivalent to those described herein can also be used in the practice or testing of the present inventions disclosed, representative illustrative methods and materials are described herein.

Enantiomeric excess (ee) is a measurement of purity used for chiral substances. It reflects the degree to which a sample contains one enantiomer in greater amounts than the other. A racemic mixture has an ee of 0%, while a single completely pure enantiomer has an ee of 100%. A sample with 70% of one enantiomer and 30% of the other has an ee of 40% (70%-30%). A sample of a chemical is considered enantiopure (also termed enantiomerically pure) when it has, within the limits of detection, molecules of only one chirality. As used herein refers to a composition exhibiting an enantiomeric excess of at least 99%.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes separate embodiments where a non-hydrogen substituent is present and those where a non-hydrogen substituent is not present.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1: General Information

Unless noted in the specific procedure, reactions were performed in flame-dried glassware under argon atmosphere. All metathesis reactions were carried out under air-free conditions in dry glassware in a Vacuum Atmospheres Glovebox filled with $N_2$. General solvents were purified by passing through solvent purification columns. Commercially available substrates were used as received. All solvents and substrates were sparged with Ar before bringing into the glovebox and filtered over basic alumina (Brockmann I) prior to use. Reaction progress was monitored by thin layer chromatography (TLC) using E. Merck silica gel 60 F254 precoated plates (0.25 mm) and visualized by UV fluorescence quenching, potassium permanganate, or p-anisaldehyde staining. Silicycle SiliaFlash P60 Academic Silica gel (particle size 0.040-0.063 mm) was used for flash chromatography. Analytical chiral IPLC was performed with an Agilent 1100 Series HPLC utilizing Chiralcel OD-H and OJ-H columns (4.6 mm×25 cm) obtained from Daicel Chemical Industries, Ltd. with visualization at 254 nm. Analytical SFC was performed with a Mettler SFC supercritical CO2 analytical chromatography system utilizing Chiralcel OD-H column (4.6 mm×25 cm) obtained from Daicel Chemical Industries, Ltd. with visualization at 210 nm. GC conversion data was obtained using an HP-5 capillary column with an Agilent 6850 FID gas chromatograph. $^1$H and $^{13}$C NMR spectra were recorded on a Varian Inova 500 spectrometer (500 MHz and 126 MHz, respectively), a Bruker AV III HD spectrometer equipped with a Prodigy liquid nitrogen temperature cryoprobe (400 MHz and 101 MHz, respectively), or a Varian Mercury 300 spectrometer (300 MHz and 75 MHz, respectively) and are reported in terms of chemical shift relative to residual CHCl$_3$ (δ 7.26 and δ 77.16 ppm, respectively). Data for $^1$H NMR spectra are reported as follows: chemical shift (S ppm) (multiplicity, coupling constant (Hz), integration). Abbreviations are used as follows: s=singlet, bs=broad singlet, d=doublet, t=triplet, q=quartet, quint=quintet, m=complex multiplet. Infrared (IR) spectra were recorded on a Perkin Elmer Paragon 1000 spectrometer using neat samples on ATR diamond, and are reported in frequency of absorption (cm$^{-1}$). High-resolution mass spectra HRMS were acquired from the Caltech Mass Spectral Facility using fast-atom bombardment (FAB+), electrospray ionization (TOF ES+) or electron impact (EI+), and an Agilent 6200 Series TOF with an Agilent G1978A Multimode source in electrospray ionization (ESI), atmospheric pressure chemical ionization (APCI), or mixed (MM) ionization mode. Optical rotations were measured on a Jasco P-2000 polarimeter using a 100 mm pathlength cell at 589 nm.

The following reactions (as represented in the various embodiments set forth in the descriptions and Figures) carried out under inert atmosphere (nitrogen or argon) at temperatures varying from −20° C. to 40° C. The reaction times varies from several minutes to several hours, depending in part on the nature of the compositions or in some cases merely for convenience. Several representative examples described as follows, though these procedures can be modified as would be appreciated by those skilled in the art, and so should be considered exemplary rather than limiting.

Example 2. Experimental Procedures and Characterization Data

The readers is referred to FIGS. 7-11 for the schemes associated with these procedures Example 2. 1. Preparation of (±)-6

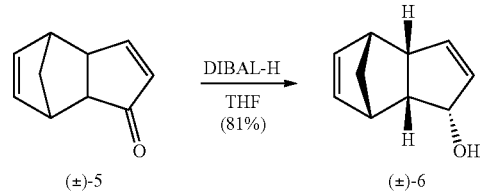 [SMILES: O=C1C=CC2C3C=CC(C3)C12 ; O[C@H]1C=C[C@@H]2[C@H]1[C@@H]1C=C[C@H]2C1]

Racemic enone (±)-5 was obtained from photooxygenation of dicyclopentadiene catalyzed by tetraphenylporphyrin (TPP) according to Mihelich, E. D., et al., *J. Org. Chem.* 1983, 48, 4135-4137. In a 500 mL round bottom flask, (±)-5 (13.2 g, 8.9 mmol) was dissolved in anhydrous toluene (150 mL) under argon atmosphere. The solution was cooled to −78° C., and a solution of DIBAL-H (1.0 M solution in toluene, 13.4 mL, 13.4 mmol, 1.5 equiv) was added dropwise. After 1.5 h, MeOH (50 mL) was added (dropwise at beginning to avoid splashing). The reaction mixture was warmed to ambient temperature, poured into a saturated Na—K tartrate solution (150 mL), and the biphasic solution was stirred overnight. The aqueous phase was extracted with CH$_2$C12 (3×200 mL). The combined organic phases were dried with anhydrous magnesium sulfate, filtered, and concentrated under reduced pressure. Purification by flash column chromatography on silica gel (SiO$_2$, 10:1 to 4:1 hexanes/EtOAc) afforded compound(I)-6 as a white solid (10.9 g, 81% yield).

TLC (4:1 hexanes/EtOAc): R$_f$=0.3 (KMnO$_4$).

$^1$H NMR (400 MHz, CDCl$_3$): δ 6.15 (dd, J=5.7, 2.6 Hz, 1H), 5.81 (dd, J=5.7, 3.2 Hz, 1H), 5.59 (s, 2H), 4.67 (t, J=9.0 Hz, 1H), 3.29 (dd, J=7.6, 4.1 Hz, 1H), 2.99-2.87 (m, 3H), 1.51 (ddt, J=46.0, 8.0, 1.6 Hz, 2H), 1.23 (d, J=9.6 Hz, 1H)

Example 2.2. Enzymatic Kinetic Resolution

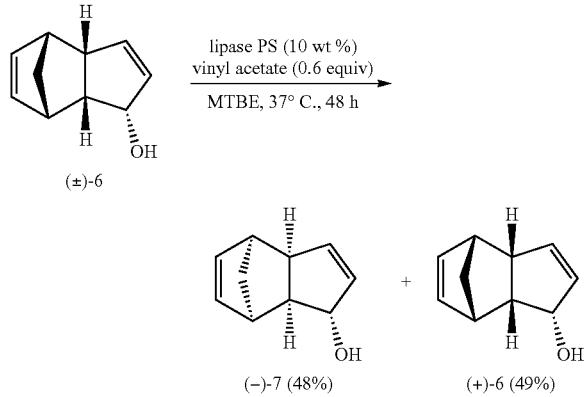

In a 250 mL round bottom flask, (±)-6 (4.8 g, 32.4 mmol) was dissolved in MTBE (100 mL, 0.33 M), and vinyl acetate (1.78 mL, 19.4 mmol, 0.6 equiv) was added via syringe. Lipase PS (10% on celite, 480 mg, 10 wt %) was added to the flask. The flask was sealed with a septum and kept under argon atmosphere and placed in 37° C. oil bath. After 48 h, the reaction mixture was filtered through celite and concentrated. Column chromatography (SiO$_2$, 10:1 to 4:1 hexanes/EtOAc) afforded white solids (−)-7 (2.93 g, 48% yield) and (+)-6 (2.36 g, 49% yield).

For (−)-7: TLC (10:1 hexanes/EtOAc): Rf=0.68 (KMnO$_4$).

For (−)-7: $^1$H NMR (400 MHz, CDCl3): δ 5.98 (dd, J=5.7, 2.9 Hz, 1H), 5.76 (dd, J=5.6, 3.1 Hz, 1H), 5.70 (dt, J=5.8, 2.0 Hz, 1H), 5.55 (dt, J=5.8, 1.9 Hz, 1H), 5.44 (dq, J=9.0, 1.7 Hz, 1H), 3.28 (ddt, J=7.6, 3.5, 1.7 Hz, 1H), 3.08 (ddd, J=8.9, 7.7, 4.1 Hz, 1H), 2.89 (ddp, J=4.3, 2.9, 1.3 Hz, 1H), 2.76 (s, 1H), 2.07 (s, 3H), 1.46 (ddt, J=39.3, 8.2, 1.7 Hz, 2H).

For (+)-6: TLC (10:1 hexanes/EtOAc): Rf=0.28 (KMnO$_4$).

For (+)-6: $^1$H NMR spectrum data matched (±)-6.

For (+)-6: $[α]_D^{23}$: +117.9° (c=1.0, CHCl$_3$).

Example 2.3. Preparation of Enone (+)-5

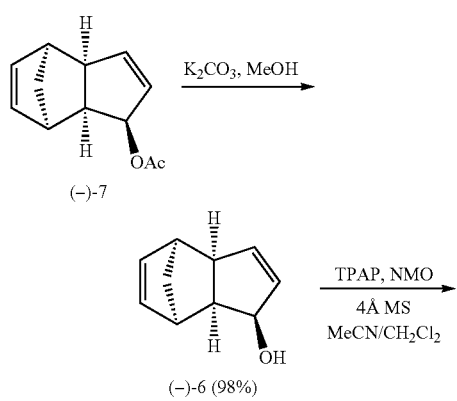

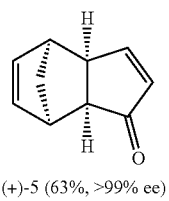

To a stirred solution of (−)-7 (2.8 g, 14.7 mmol) in MeOH (50 mL) was added K$_2$CO$_3$ (2.03 g, 14.7 mmol, 1 equiv). The solution was stirred for 12 h and was concentrated, then dissolved in water (30 mL) and extracted by Et$_2$O (30 mL). Column chromatography (SiO$_2$, 4:1 hexanes/EtOAc) afforded (−)-6 as a white solid (2.04 g, 98%). Spectrum data matched (±)-6. $[α]_D^{23}$: −138.1 (c=1.0, CHCl$_3$).

A 100 mL round bottom flask containing 4A molecular sieves (9.0 g) was flame-dried under vacuum. (−)-6 (2.01 g, 13.6 mmol) and NMO (N-methylmorpholine N-oxide, 3.19 g, 27.2 mmol, 2 equiv) were added and dissolved in MeCN (3 mL) and CH$_2$Cl$_2$ (27 mL). TPAP (Tetra-n-propylammonium perruthenate, 150 mg, 0.42 mmol, 0.03 equiv) was then added and the reaction was stirred under argon for 1 hour, and the reaction progress was monitored by GC. The reaction mixture was filtered over celite and concentrated. Column chromatography (SiO$_2$, 4:1 hexanes/EtOAc) afforded (+)-5 as a white solid (1.24 g, 63%). NMR spectrum data matched (+)-5.

TLC (4:1 hexanes/EtOAc): Rf=0.35 (UV).

$^1$H NMR (400 MHz, CDCl3): δ 7.38 (dd, J=5.7, 2.6 Hz, 1H), 5.95 (ddd, J=7.8, 5.6, 2.3 Hz, 2H), 5.78 (dd, J=5.7, 3.0 Hz, 1H), 3.42 (dddd, J=5.6, 4.2, 2.6, 1.6 Hz, 1H), 3.22 (dt, J=4.1, 1.8 Hz, 1H), 2.97 (ddt, J=4.2, 2.7, 1.4 Hz, 1H), 2.80 (t, J=5.1 Hz, 1H), 1.68 (dd, J=54.4, 8.4 Hz, 2H).

$^{13}$C NMR (101 MHz, CDCl$_3$): δ 210.9, 164.7, 137.1, 132.7, 52.9, 50.4, 48.4, 45.1, 44.2.

FTIR (ATR): 2990. 2972, 1683, 1576, 1347, 1333, 1294, 1251, 1224, 1194, 1178, 1120, 1091, 1018, 959, 853, 817, 784, 739, 721, 652 cm$^{-1}$.

HRMS (FAB+, m/z): calc'd for C$_{10}$H$_{11}$O [M+H]$^+$ 147.0810, found: 147.0809.

$[α]_D^{23}$: +136.6° (c=1.0, CHCl$_3$).

Example 2.4. Preparation of Enone (−)-5

A. Oxidation with TPAP, NMO

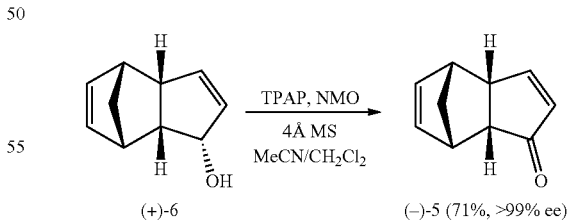

A 100 mL round bottom flask containing 4A molecular sieves (9.0 g) was flame-dried under vacuum. (+)-6 (2.00 g, 13.5 mmol) and NMO (3.16 g, 27 mmol, 2 equiv) were added and dissolved in MeCN (3 mL) and CH$_2$Cl$_2$ (27 mL). TPAP (142 mg, 0.41 mmol, 0.03 equiv) was then added and the reaction was stirred under argon for 1 hour, and the reaction progress was monitored by GC. The reaction mixture was filtered over celite and concentrated. Column chromatography (SiO$_2$, 4:1 hexanes/EtOAc) afforded (−)-5 as a white solid (1.41 g, 71%).

B. Oxidation Using Stahl's Conditions:

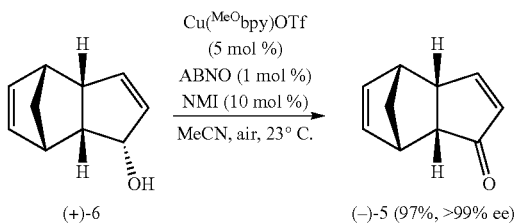 [SMILES: O[C@H]1C=C[C@@H]2[C@H]1[C@@H]1C=C[C@H]2C1 ; O=C1C=C[C@@H]2[C@H]1[C@@H]1C=C[C@H]2C1]

An oven-dried, 200 mL round-bottomed flask was charged with alcohol (+)-6 (2.01 g, 13.6 mmol, 1.0 equiv) and anhydrous MeCN (100 mL). The solution was vigorously stirred (>700 rpm) open to air while being treated with $^{MeO}$bpy (147 mg, 0.68 mmol, 0.05 equiv), Cu(MeCN)$_4$OTf (256 mg, 0.68 mmol, 0.05 equiv), ABNO (9-Azabicyclo[3.3.1]nonane N-Oxyl, 0.04 M in MeCN, 3.4 mL, 135.6 µmol, 0.01 equiv), and then NMI (N-methylimidazole, 110 µL, 1.36 mmol, 0.10 equiv) via microsyringe. The resulting brick-red reaction mixture was vigorously stirred and exposed to air at ambient temperature until the reaction mixture turned blue-green in an hour, at which point TLC analysis indicated the complete consumption of starting material. The reaction mixture was diluted with Et$_2$O (50 mL), and filtered through Celite, washing with 50% EtOAc/hexanes. The filtrate was concentrated in vacuo and the crude residue was directly purified by flash chromatography (SiO$_2$, 4:1 hexanes/EtOAc) to afford (−)-5 (1.92 g, 97% yield) as a white solid.

Within the context of this transformation, other source of Cu(CH$_3$CN)$_4$$^+$ may be considered (e.g., having counterions of mesylate, triflate, tosylate, BF$_4$$^-$, PF$_6$$^-$, SbF$_6$$^-$, etc.) in concert with other co-catalysts including TEMPO and other bipyridines, as well as the ABNO and NMI recited above.

TLC (4:1 hexanes/EtOAc): Rf=0.35 (UV).

$^1$H NMR spectrum data matched (+)-5.

[α]$_D$$^{23}$: −121.9° (c=1.0, CHCl$_3$).

HPLC Conditions: 5% IPA, 1.0 mL/min, Chiralcel OJ-H column, λ=254 nm, t$_R$(min)=7.8 ((−)-5), 8.3 ((+)-5)

Example 2.5. Preparation of (+)- and (−)-8

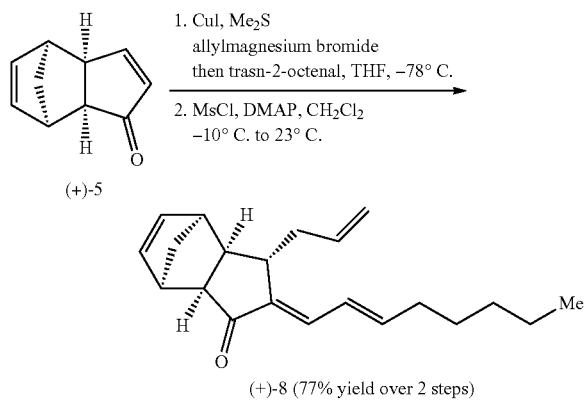

A 250 mL flask was charged with CuI (2.56 g, 13.44 mmol, 1.2 equiv) and flame-dried under vacuum. After cooling to room temperature, anhydrous THF (100 mL) and Me$_2$S (5 mL) were added, and the solution was vigorously stirred for 5 minutes at room temperature until a yellow homogeneous solution was formed. At −78° C., allylmagnesium bromide (12.3 mL, 1.0 M solution in THF, 12.3 mmol, 1.1 equiv) was added slowly. The reaction mixture was stirred at −78° C. for 1 hour and a solution of (+)-5 (1.637 g, 11.2 mmol, 1.0 equiv) in THF (5 mL) was added slowly. After 30 minutes stirring at the same temperature, a solution of trans-2-octenal (2.826 g, 22.4 mmol, 2.0 equiv) in THF (3 mL) was added slowly. The reaction was stirred for additional 1 hour at −78° C., and a solution of saturated NH$_4$Cl and NH$_3$.H$_2$O (100 mL, 9:1 NH$_4$Cl/NH$_3$.H$_2$O) was added. The biphasic solution was warmed to room temperature and was vigorously stirred until a homogeneous dark blue solution was formed in the aqueous phase. The phases were separated and the organic phase was washed with 20 mL saturated NH$_4$Cl solution. The combined aqueous phase was extracted with Et$_2$O (3×100 mL). The combined organic phase was dried with anhydrous magnesium sulfate and was concentrated in vacuo. The residue was purified by flash chromatography (SiO$_2$, hexanes/EtOAc 15:1) to give a mixture of diastereomers of the aldol products (3.6 g).

A portion of the reaction mixture was taken out and the major diastereomer was isolated as follow:

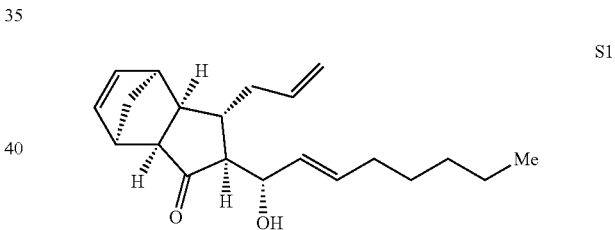

S1

TLC (4:1 hexanes/EtOAc): Rf=0.33 (p-anisaldehyde).

$^1$H NMR (400 MHz, CDCl$_3$): δ 6.18 (dd, J=5.7, 2.9 Hz, 1H), 6.10 (dd, J=5.8, 3.0 Hz, 1H), 5.80 (dddd, J=15.7, 11.0, 8.1, 6.1 Hz, 1H), 5.63 (dt, J=15.3, 6.7 Hz, 1H), 5.30 (ddt, J=15.3, 8.0, 1.6 Hz, 1H), 5.13-5.06 (m, 2H), 4.18 (d, J=1.9 Hz, 1H), 4.04 (td, J=8.2, 1.9 Hz, 1H), 3.19 (ddt, J=4.5, 3.0, 1.4 Hz, 1H), 3.09 (ddd, J=10.2, 4.7, 2.4 Hz, 1H), 2.98 (tt, J=2.9, 1.6 Hz, 1H), 2.64 (ddd, J=9.9, 5.6, 4.1 Hz, 1H), 2.40 (dddd, J=13.3, 5.5, 3.8, 1.7 Hz, 1H), 2.12-1.97 (m, 4H), 1.57 (dt, J=8.4, 1.8 Hz, 1H), 1.51-1.42 (m, 2H), 1.41-1.22 (m, 6H), 0.87 (t, J=6.9 Hz, 3H).

$^{13}$C NMR (101 MHz, CDCl$_3$): δ 136.3, 135.8, 134.0, 129.8, 117.2, 73.1, 61.8, 56.6, 52.5, 47.2, 45.9, 45.5, 40.9, 40.4, 32.3, 31.6, 28.8, 22.6, 14.1. (The carbonyl peak was not observed below 219 ppm)

FTIR (ATR): 3465, 3073, 2957, 2925, 2857, 1709, 1640, 1600, 1439, 1413, 1338, 1249, 1224, 1090, 973, 911, 836, 733 cm$^{-1}$.

HRMS (FAB+, m/z): calc'd for C$_{21}$H$_{29}$O$_2$ [M+H−H2]$^+$ 313.2168, found: 313.2158.

[α]$_D$$^{23}$: +28.1° (c=1.0, CHCl$_3$).

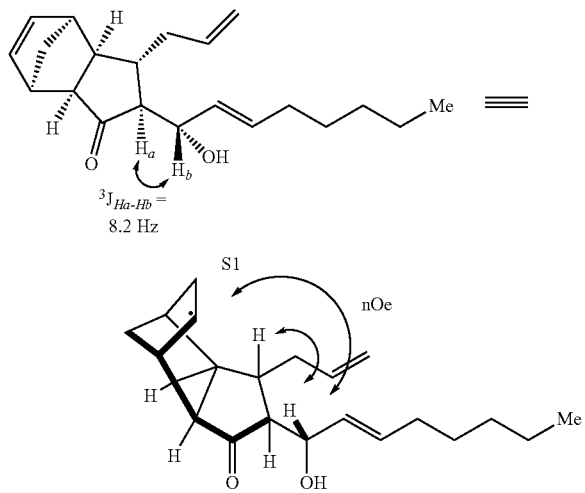

Kobayashi et al. (*J. Org. Chem.* 2002, 67, 7110-7123) established that for compounds S1 (anti-aldols), $^3J_{Ha-Hb}$ is in the range of 8.4 to 9.7 Hz, while for the corresponding syn-aldols $^3J_{Ha-Hb}$ is around 3 Hz. The stereochemistry of H$_b$ was also confirmed by nOe analysis of S.

Without further separation, the crude aldol product was dissolved in CH$_2$Cl$_2$ (200 mL) and cooled to 0° C. DMAP (4-dimethylaminopyridine, 20.5 g, 168 mmol, 15.0 equiv) and MsCl (2.6 mL, 33.6 mmol, 3.0 equiv) were added sequentially. The reaction mixture was slowly warmed to room temperature and was stirred for 16 h before washed with 1 M HCl (100 mL). The aqueous phase was extracted with EtOAc (3×100 mL). The combined organic phase was dried with anhydrous magnesium sulfate and was concentrated in vacuo. The residue was purified by flash chromatography (hexanes/EtOAc 20:1) to give (+)-8 (2.55 g, 77% yield over 2 steps) as a yellow liquid.

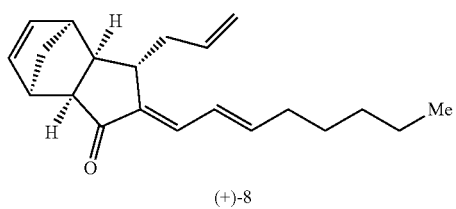 [SMILES: C=CC[C@@H]1/C(=C\C=C\CCCCC)C(=O)[C@@H]2[C@H]1[C@@H]1C=C[C@H]2C1]

(+)-8

TLC (10:1 hexanes/EtOAc): Rf=0.48 (UV).

$^1$H NMR (400 MHz, CDCl$_3$): δ 6.70 (dd, J=10.7, 2.1 Hz, 1H), 6.20-6.04 (m, 2H), 5.97 (qd, J=5.6, 2.7 Hz, 2H), 5.79 (ddt, J=17.1, 10.2, 6.9 Hz, 1H), 5.14-5.05 (m, 2H), 3.24 (tq, J=2.8, 1.4 Hz, 1H), 3.01 (dp, J=4.4, 1.4 Hz, 1H), 2.97 (dd, J=8.6, 4.8 Hz, 1H), 2.64-2.56 (m, 2H), 2.35-2.26 (m, 1H), 2.22-2.07 (m, 3H), 1.49-1.37 (m, 4H), 1.35-1.23 (m, 4H), 0.89 (t, J=6.8 Hz, 3H).

$^{13}$C NMR (101 MHz, CDCl$_3$): δ 209.8, 146.8, 141.1, 136.1, 136.0, 133.5, 132.7, 126.3, 117.1, 54.0, 51.5, 47.4, 47.2, 43.7, 41.2, 40.3, 33.5, 31.4, 28.5, 22.5, 14.0.

FTIR (ATR): 3062, 2957, 2928, 2858, 1701, 1625, 1600, 1438, 1341, 1293, 1202, 1178, 1122, 973, 912, 727, 698 cm$^{-1}$.

HRMS (FAB+, m/z): calc'd for C$_{21}$H$_{29}$O [M+H]$^+$ 297.2218, found: 297.2214.

[α]$_D^{23}$: +150.4° (c=1.0, CHCl$_3$).

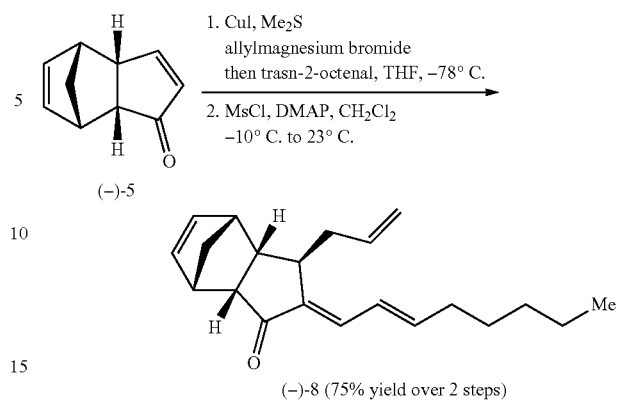

A 250 mL flask was charged with CuI (571 mg, 3 mmol, 1.2 equiv) and flame-dried under vacuum. After cooling to room temperature, anhydrous THF (25 mL) and Me$_2$S (1 mL) were added, and the solution was vigorously stirred for 5 minutes at room temperature until a yellow homogeneous solution was formed. At −78° C., allylmagnesium bromide (2.75 mL, 1.0 M solution in THF, 2.75 mmol, 1.1 equiv) was added slowly. The reaction mixture was stirred at −78° C. for 1 hour and a solution of (−)-5 (365 mg, 2.5 mmol, 1.0 equiv) in THF (2 mL) was added slowly. After 30 minutes stirring at the same temperature, a solution of trans-2-octenal (631 mg, 5.0 mmol, 2.0 equiv) in THF (1 mL) was added slowly. The reaction was stirred for additional 1 hour at −78° C., and a solution of saturated NH$_4$Cl and NH$_3$.H$_2$O (25 mL, 9:1 NH$_4$Cl/NH$_3$.H$_2$O) was added. The biphasic solution was warmed to room temperature and was vigorously stirred until a homogeneous dark blue solution was formed in the aqueous phase. The phases were separated and the organic phase was washed with 10 mL saturated NH4Cl solution. The combined aqueous phase was extracted with Et$_2$O (3×30 mL). The combined organic phase was dried with anhydrous magnesium sulfate and was concentrated in vacuo. The residue was purified by flash chromatography (SiO$_2$, hexanes/EtOAc 15:1) to give a mixture of diastereomers of the aldol products (790 mg).

Without further separation, the crude aldol product was dissolved in CH$_2$Cl$_2$ (40 mL) and cooled to 0° C. DMAP (4.58 g, 37.5 mmol, 15.0 equiv) and MsCl (0.58 mL, 7.5 mmol, 3.0 equiv) were added sequentially. The reaction mixture was slowly warmed to room temperature and was stirred for 16 h before washed with 1 M HCl (40 mL). The aqueous phase was extracted with EtOAc (3×40 mL). The combined organic phase was dried with anhydrous magnesium sulfate and was concentrated in vacuo. The residue was purified by flash chromatography (hexanes/EtOAc 20:1) to give (−)-8 (559 mg, 75% yield over 2 steps) as a yellow liquid. Characterization data matched (+)-8. [α]$_D^{23}$: −193.4° (c=1.0, CHCl$_3$).

Example 2.6. Preparation of (+)- and (−)-9

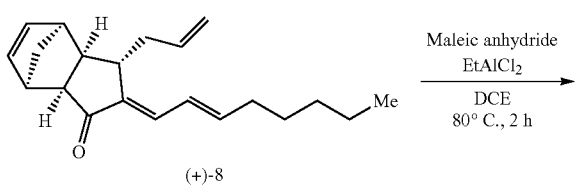

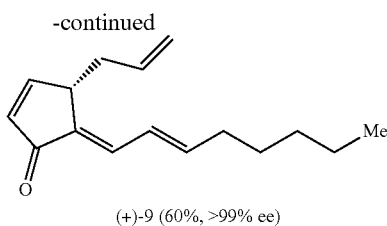

(+)-9 (60%, >99% ee)

In a 100 mL round bottom flask, (+)-8 (1.64 g, 5.54 mmol, 1.0 equiv) was dissolved in DCE (dichloroethane, 50 mL). Maleic anhydride (5.4 g, 55.4 mmol, 10.0 equiv) and EtAlCl$_2$ (6.0 mL, 1.0 M solution in hexanes, 6.0 mmol, 1.1 equiv) were added sequentially. A reflux condenser was attached and the reaction mixture was warmed to reflux under argon. After 2 hours, the reaction mixture was cooled down, concentrated and directly loaded on silica gel. Purification by flash chromatography (hexanes/EtOAc 15:1) afforded (+)-9 (760 mg, 60% yield, >99% ee by chiral HPLC analysis) as a colorless liquid. Spectral data ($^1$H NMR, $^{13}$C NMR, HRMS, IR) matched with the published data (Li, J., et al., *J. Am. Chem. Soc.*, 2019, 141, 154-158).

TLC (4:1 hexanes/EtOAc): Rf=0.56 (UV).

$^1$H NMR (300 MHz, CDCl$_3$): δ 7.50 (ddd, J=6.0, 2.6, 1.0 Hz, 1H), 6.95 (dt, J=10.7, 1.2 Hz, 1H), 6.35 (dd, J=6.0, 1.8 Hz, 1H), 6.33-6.15 (m, 2H), 5.81-5.64 (m, 1H), 5.11-5.01 (m, 2H), 3.60 (ddq, J=8.5, 4.1, 1.9 Hz, 1H), 2.73-2.58 (m, 1H), 2.24 (dddd, J=13.4, 9.7, 6.8, 1.5 Hz, 3H), 1.54-1.37 (m, 2H), 1.38-1.22 (m, 4H), 0.96-0.84 (t, J=6.9 Hz, 3H).

$^{13}$C NMR (75 MHz, CDCl$_3$): δ 197.5, 160.6, 147.1, 135.4, 134.9, 134.3, 131.8, 125.7, 117.8, 43.2, 37.4, 33.6, 31.5, 28.6, 22.6, 14.1.

FTIR (ATR): 2956, 2926, 2856, 1692, 1631, 1580, 1440, 1338, 1280, 1207, 1102, 977, 915, 871, 839, 801, 753, 730, 666 cm$^{-1}$.

HRMS (FAB+, m/z): calc'd for C$_{16}$H$_{21}$O [M+H−H2]$^+$ 229.1586, found: 229.1581.

[α]$_D^{23}$: +150.4° (c=1.0, CHCl$_3$).

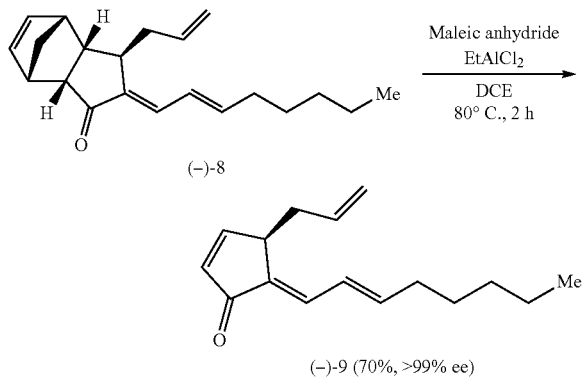

(−)-9 (70%, >99% ee)

In a 50 mL round bottom flask, (−)-8 (667 mg, 2.25 mmol, 1.0 equiv) was dissolved in DCE (20 mL). Maleic anhydride (2.2 g, 22.5 mmol, 10.0 equiv) and EtAlCl$_2$ (2.5 mL, 1.0 M solution in hexanes, 2.5 mmol, 1.1 equiv) were added sequentially. A reflux condenser was attached and the reaction mixture was warmed to reflux under argon. After 2 hours, the reaction mixture was cooled down, concentrated and directly loaded on silica gel. Purification by flash chromatography (hexanes/EtOAc 15:1) afforded (−)-9 (361 mg, 70% yield, >99% ee by chiral HPLC analysis) as a colorless liquid. Characterization data matched (+)-9.

[α]$_D^{23}$: −122.9° (c=1.0, CHCl$_3$).

HPLC Conditions: 5% IPA, 1.0 mL/min, Chiralcel OD-H column, λ=254 nm, t$_R$(min)=5.9 ((+)9), 8.2-8.3 ((−)-9)

Example 2.7. Preparation of 10

A. One-pot homodimerization/stereoretentive metathesis method:

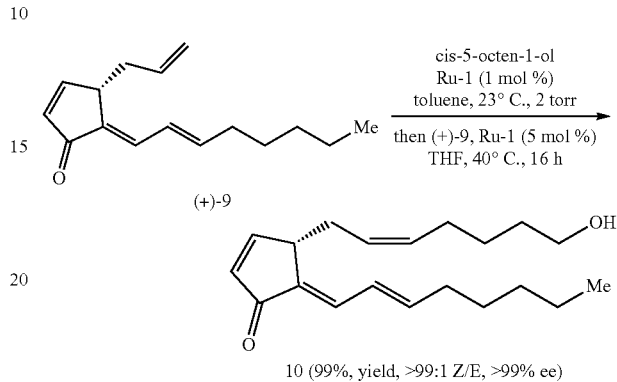

10 (99%, yield, >99:1 Z/E, >99% ee)

In a nitrogen-filled glovebox, cis-5-octen-1-ol (205 mg, 1.6 mmol, 8.0 equiv) was dissolved in toluene (2 mL) in a 50 mL Schlenk flask and a solution of catalyst Ru-1 (13.5 mg, 16 μmol, 1 mol %) in THF (0.8 mL) was added. The Schlenk flask was sealed and brought out of the glovebox, and then connected to high vacuum. The valve was gradually opened (Caution: open slowly and stir well to avoid splashing). After 15 minutes stirring, the flask was refilled with argon and sealed, and was brought back into the glovebox. The residue was diluted with THF (0.5 mL), and an aliquot was taken for GC analysis (conversion of the homodimerization step was >98% by GC analysis). A solution of (+)-9 (46 mg, 0.2 mmol, 1.0 equiv) in THF (0.5 mL) was added into the Schlenk flask and an additional portion of catalyst Ru-1 (8.5 mg, 10 mol, 5 mol %) solution in THF (0.5 mL) was added. The Schlenk flask was sealed and brought out of glovebox. The reaction was stirred for 16 h at 40° C. before being quenched with a few drops of ethyl vinyl ether. The solvent was removed under reduced pressure. The residue was purified by flash chromatography (hexanes/EtOAc 2:1) to give 10 (60 mg, 99%, >99:1 Z/E, >99% ee by chiral HPLC analysis). Spectral data (H NMR, $^{13}$C NMR, HRMS, IR) matched with the published data.

TLC (4:1 hexanes/EtOAc): Rf=0.2 (UV).

$^1$H NMR (400 MHz, CDCl3): δ 7.48 (ddd, J=6.0, 2.6, 1.0 Hz, 1H), 6.95 (dt, J=11.0, 1.3 Hz, 1H), 6.34-6.19 (m, 3H), 5.52-5.44 (m, 1H), 5.38-5.30 (m, 1H), 3.63 (t, J=6.5 Hz, 2H), 3.60-3.55 (m, 1H), 2.60 (dddd, J=14.0, 6.2, 4.3, 1.4 Hz, 1H), 2.30 (dtd, J=14.4, 8.6, 1.2 Hz, 1H), 2.25-2.17 (m, 2H), 2.01 (qd, J=7.3, 1.4 Hz, 2H), 1.59-1.49 (m, 3H), 1.48-1.37 (m, 4H), 1.34-1.29 (m, 4H), 0.89 (t, J=7.0 Hz, 3H).

$^{13}$C NMR (101 MHz, CDCl$_3$): δ 197.6, 160.9, 147.0, 135.4, 135.3, 132.6, 131.8, 125.8, 125.3, 62.9, 43.7, 33.6, 32.5, 31.5, 30.9, 28.6, 27.2, 25.8, 22.6, 14.2.

FTIR (ATR): 3445, 2960, 2930, 2862, 1690, 1629, 1580, 1447, 1264, 1207, 1054, 979, 732 cm$^{-1}$.

HRMS (TOF, ES+, m/z): calc'd for C$_2$H$_{31}$O$_2$ [M+H]$^+$ 303.2319, found: 303.2320.

[α]$_D^{23}$: +142.6° (c=0.5, CHCl$_3$).

HPLC Conditions: 10% IPA, 1.0 mL/min, Chiralcel OD-H column, λ=210 nm, tR (min): major=9.64, minor=13.83

B. Stereoretentive Cross-Metathesis Method:

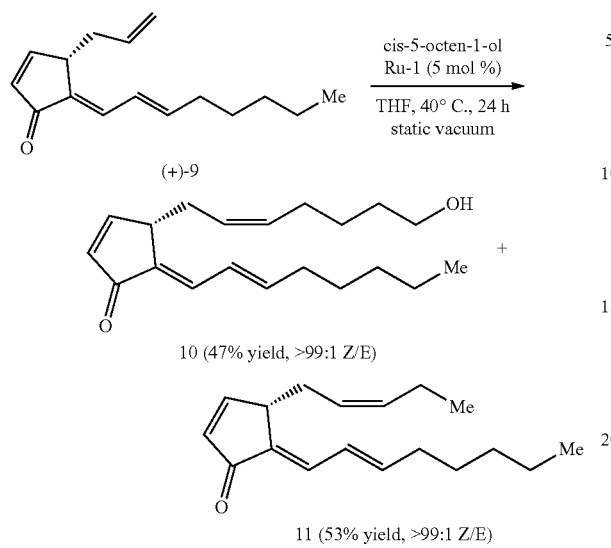

10 (47% yield, >99:1 Z/E)

11 (53% yield, >99:1 Z/E)

In a nitrogen-filled glovebox, (+)-9 (49 mg, 0.21 mmol, 1.0 equiv) and cis-5-octen-1-ol (205 mg, 1.6 mmol, 7.6 equiv) were dissolved in THF (0.5 mL) in a 1-dram vial, and the solution was transferred to a 50 mL Schlenk flask. A solution of catalyst Ru-1 (8.5 mg, 10 mol, 5 mol %) in THF (0.5 mL) was added. The Schlenk flask was sealed and brought out of the glovebox, and freeze-pump-thaw for one time to keep it under static vacuum. The reaction was stirred for 16 h at 40° C. before being quenched with a few drops of ethyl vinyl ether. The solvent was removed under reduced pressure. The residue was purified by flash chromatography (hexanes/EtOAc 10:1 to 2:1) to give 10 (30 mg, 47%, >99:1 Z/E) and 11 (29 mg, 53%, >99:1 Z/E) as two major products.

11

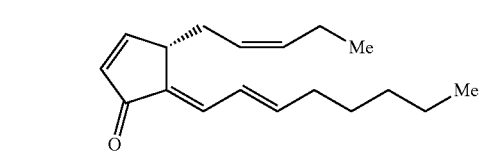

TLC (4:1 hexanes/EtOAc): Rf=0.6 (UV).

$^1$H NMR (400 MHz, CDCl$_3$): δ 7.48 (ddd, J=5.9, 2.6, 1.0 Hz, 1H), 6.95 (dt, J=11.2, 1.2 Hz, 1H), 6.39-6.17 (m, 3H), 5.53-5.43 (m, 1H), 5.34-5.24 (m, 1H), 3.56 (ddq, J=8.6, 4.1, 2.0 Hz, 1H), 2.70-2.47 (m, 1H), 2.34-2.17 (m, 3H), 1.99 (pd, J=7.5, 1.6 Hz, 2H), 1.46 (p, J=7.3 Hz, 2H), 1.31 (tt, J=5.6, 2.8 Hz, 4H), 0.93 (t, J=7.6 Hz, 3H), 0.89 (t, J=6.9 Hz, 3H).

$^{13}$C NMR (101 MHz, CDCl$_3$): δ 197.6, 160.9, 146.8, 135.4, 134.6, 131.7, 125.8, 124.3, 43.8, 33.6, 31.5, 30.8, 28.6, 22.6, 20.8, 14.3, 14.1.

FTIR (ATR): 2959, 2927, 2856, 2360, 1693, 1632, 1579, 1459, 1376, 1337, 1294, 1203, 1100, 1069, 1020, 976, 923, 867, 834, 805, 728, 668 cm$^{-1}$.

HRMS (ESI, m/z): calc'd for C18H27O [M+H]+ 259.2056, found: 259.2207.

$[α]_D^{23}$: +210.8° (c=1.0, CHCl$_3$).

Example 2.8. Preparation of 15-deoxy-Δ12,14-prostaglandin J2 (2)

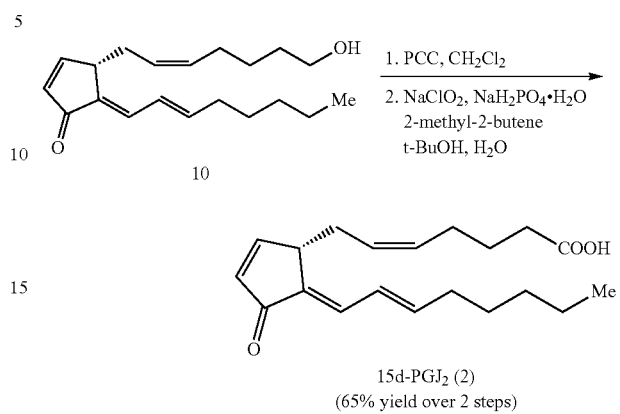

15d-PGJ$_2$ (2)
(65% yield over 2 steps)

Pyridinium chlorochromate (129 mg, 0.6 mmol, 3.0 equiv) was added to a solution of 10 (60 mg, 0.2 mmol, 1.0 equiv) in CH$_2$Cl$_2$ (2 mL) at room temperature. The reaction progress was monitored by TLC. The reaction mixture was diluted with Et$_2$O (2 mL) after stirring for 1 h. The resulting solution was filtered through a short pad of celite, concentrated, and subjected to the next step without further purification.

The residue was dissolved in t-BuOH (3 mL) at room temperature, 2-methyl-2-butene (210 μL, 2.0 mmol, 10 equiv), a solution of NaH$_2$PO$_4$.H$_2$O (41.4 mg, 0.3 mmol, 1.5 equiv) in H$_2$O (0.72 mL), and a solution of NaClO$_2$ (80%, 33.6 mg, 0.3 mmol, 1.5 equiv) in H$_2$O (0.72 mL) were added sequentially. After stirring at room temperature for 30 minutes, the reaction mixture was diluted with a solution of NaH$_2$PO$_4$.H$_2$O (648 mg) in H$_2$O (12 mL) and was extracted with EtOAc (5×10 mL). The combined organic extracts were dried over anhydrous magnesium sulfate, filtered, and concentrated under reduced pressure. Flash column chromatography (SiO$_2$, CH$_2$Cl$_2$/MeOH 20:1) afforded pure compound 2 (41.0 mg, 65% yield over 2 steps) as a colorless oil. Spectral data (H NMR, 13C NMR, HRMS, IR) matched with the published data.

TLC (100% EtOAc): Rf=0.70 (UV).

$^1$H NMR (400 MHz, CDCl$_3$): δ 7.47 (dd, J=6.0, 2.5 Hz, 1H), 6.95 (d, J=11.0 Hz, 1H), 6.38-6.19 (m, 3H), 5.50-5.33 (m, 2H), 3.62-3.55 (m, 1H), 2.63-2.55 (m, 1H), 2.38-2.26 (m, 3H), 2.23 (q, J=7.1 Hz, 2H), 2.05 (q, J=7.3 Hz, 2H), 1.68 (p, J=7.4 Hz, 2H), 1.46 (p, J=7.1 Hz, 2H), 1.37-1.25 (m, 4H), 0.90 (t, J=6.9 Hz, 3H).

$^{13}$C NMR (101 MHz, CDCl$_3$): δ 197.6, 177.9, 160.8, 147.2, 135.5, 135.1, 131.9, 131.5, 126.2, 125.8, 43.6, 33.6, 33.2, 31.6, 30.8, 28.6, 26.7, 24.6, 22.6, 14.2.

FTIR (ATR): 2960, 2928, 2850, 1708, 1692, 1629, 1456, 1265, 1207, 978, 734, 703 cm$^{-1}$.

HRMS (TOF, ES+, m/z): calc'd for C20H29O3 [M+H]$^+$ 317.2111, found: 317.2127.

$[α]_D^{23}$: +154.4° (c=1.0, CHCl$_3$).

Example 2.9. Preparation of
15-deoxy-Δ12,14-prostaglandin J2 methyl ester (15)

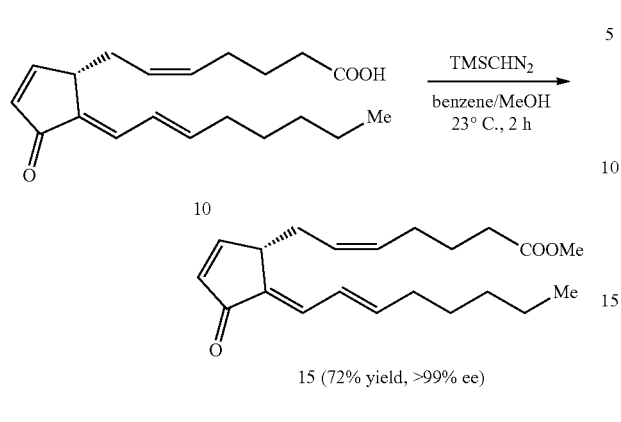

15 (72% yield, >99% ee)

In a 1-dram vial, 15d-PGJ$_2$ (2) (8.0 mg, 25 μmol, 1.0 equiv) was dissolved in C$_6$H$_6$/MeOH (3:2, 0.75 mL) at 23° C. A solution of trimethylsilyldiazomethane (20 μL, 2.0 M in hexanes, 40 μmol, 1.5 equiv) (yellow color persists). After stirring for 2 hours, the reaction mixture was concentrated under vacuum. The residue was purified by flash column chromatography (SiO2, hexanes/EtOAc, 4:1) to give 15 (6.0 mg, 72% yield, >99% ee) as a colorless oil.

TLC (4:1 hexanes/EtOAc): Rf=0.28 (UV).

$^1$H NMR (400 MHz, CDCl3): δ 7.47 (ddd, J=6.0, 2.6, 1.0 Hz, 1H), 6.95 (dt, J=11.0, 1.2 Hz, 1H), 6.37-6.17 (m, 3H), 5.50-5.31 (m, 2H), 3.66 (s, 3H), 3.57 (ddt, J=8.7, 3.8, 2.0 Hz, 1H), 2.64-2.56 (m, 1H), 2.33-2.18 (m, 5H), 2.03 (q, J=7.3 Hz, 2H), 1.66 (p, J=7.5 Hz, 2H), 1.46 (p, J=7.2 Hz, 2H), 1.31 (ddt, J=9.3, 5.3, 3.6 Hz, 4H), 0.89 (t, J=6.9 Hz, 3H).

$^{13}$C NMR (101 MHz, CDCl3): δ 197.5, 174.0, 160.8, 147.1, 135.5, 135.2, 131.8, 131.6, 126.1, 125.8, 51.7, 43.6, 33.6, 33.5, 31.6, 30.9, 28.6, 26.8, 24.8, 22.6, 14.1.

FTIR (ATR): 2953, 2927, 2856, 2360, 2342, 1736, 1694, 1632, 1579, 1436, 1364, 1205, 1090, 979, 836, 729, 668 cm$^{-1}$.

HRMS (ESI, m/z): calc'd for C$_{21}$H$_{31}$O$_3$ [M+H]$^+$ 331.2268, found: 331.2720. [α]$_D^{23}$: +72.1° (c=0.2, CHC$_3$).

SFC Conditions: 10% IPA, 4.0 mL/min, Chiralcel OD-H column, λ=254 nm, tR (min)=6.27, 7.09

Each patent, patent application, and publication cited or described in this disclosure is hereby incorporated herein by reference, each in its entirety, for all purposes, or at least for the purposes or in the context where it was cited or referenced.

What is claimed:

1. A compound of Formula (I):

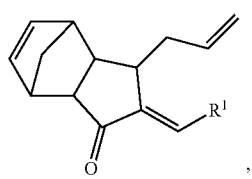

(I)

wherein: R$^1$ is one of (P-1), (P-2), (P-3), or (P-4)

(P-1)

(P-3)

(P-2)

(P-4)

R$^2$ is H or an alcohol protecting group; and at least one carbon-carbon double bond has a Z/E-selectivity of 95/5 or higher.

2. The compound of claim 1, having a structure of Formula (I-A) or (I-B):

(I-A)

(I-B)

and exhibiting an enantiomeric excess of 95% or higher.

3. A method of making a compound of Formula (I) of claim 1 by coupling an allyl group and an ω-chain to a compound of Formula (II),

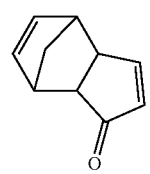

(II)

the method comprising adding to the compound of Formula (II):

(a) an organocopper allyl source and (b) an aldehyde of Formula (O-1), (O-2), (O-3), or (O-4), respectively:

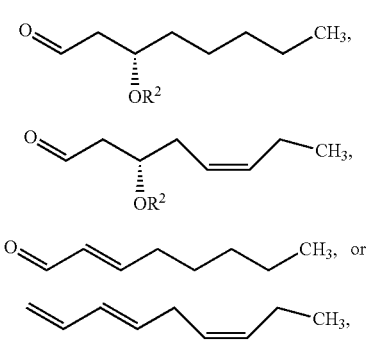

the reaction of the coupling of the compound of Formula (II), organocopper allyl source, and the aldehyde resulting in the formation of an aldol intermediate; and then
(c) oxidizing the aldol intermediate to form the compound of Formula (I) of claim 1.

4. The method of claim 3, wherein the compound Formula (II) has a structure of:

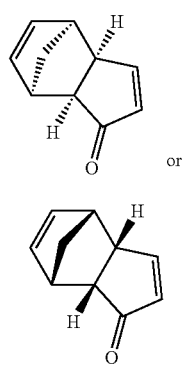

that exhibits an enantiomeric excess of 95% or higher, wherein the method results in the formation of a compound having a structure of Formula (I-A) or (I-B):

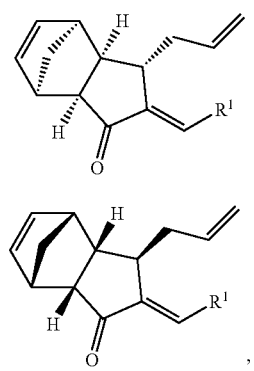

that exhibits an enantiomeric excess of 95% or higher.

5. The method of claim 4, wherein the compound of Formula (I-A) or (I-B) has an enantiomeric purity corresponding to that of the compound of Formula (II-A) or (II-B), respectively.

6. The method of claim 4, wherein the organocopper allyl source is derived from the admixture of a copper halide and an allyl Grignard reagent, optionally in the presence of an alkyl sulfide and alkali metal halide.

7. The method of claim 4, wherein oxidizing the aldol intermediate to the compound having a structure of Formula (I-A) or (I-B) comprises reacting the aldol intermediate with a sulfonylating agent and a base to form the compound of Formula (I-A) or (I-B).

8. A method of preparing a compound of Formula (VI-A) or Formula (VI-B):

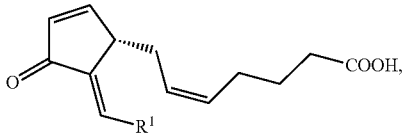

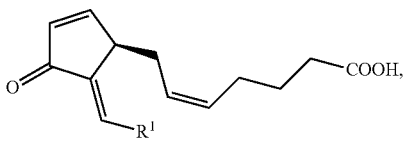

wherein $R^1$ is one of (P-1), (P-2), (P-3), or (P-4)

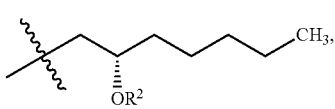

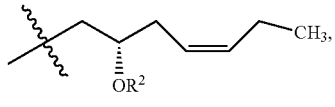

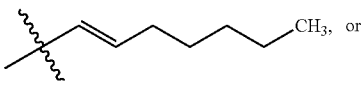

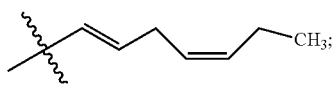

and $R^1$ is H or an alcohol protecting group;

the method comprising:
(a) subjecting a compound of Formula (I-A) or (I-B)

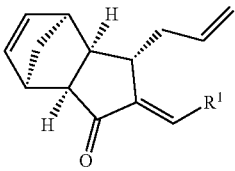

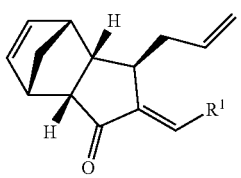

(I-B)

to conditions suitable for effecting a retro-Diels Alder reaction to form compounds corresponding to:

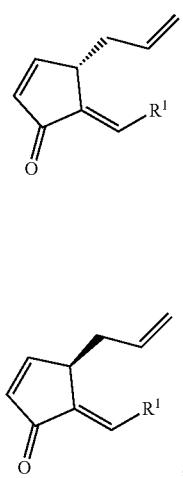

(III-A)

(III-B)

respectively.

9. The method of claim 8, wherein the conditions suitable for effecting a retro-Diels Alder reaction comprise treating the compounds of Formula (I-A) and (IB) with a Lewis acid catalyst in the optional presence of an olefin.

10. The method of claim 8 further comprising:
 (b) reacting the compound of Formula (III-A) or (III-B) with a compound of Formula (ZO-1), or (ZO-2), in the presence of a Z-selective or stereoretentive olefin metathesis catalyst:

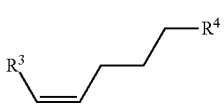

(ZO-1)

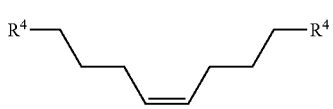

(ZO-2)

where $R^3$ is H or a $C_{1-3}$ alkyl;
$R^4$ is $CH_2$—$OR^2$, an optionally protected carboxylato (—COOH), optionally protected aldehyde (—CHO), or a cyano (—CN);

under conditions effective to cross-metathesize the compound of compound (I-A) or (I-B) with the compound of Formula (IV) to form a compound of Formula (IV-A) or (IV-B)

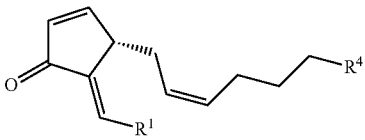

(IV-A)

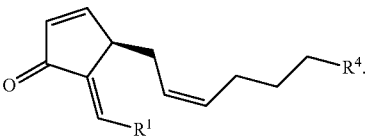

(IV-B)

11. The method of claim 10, wherein the Z-selective or stereoretentive olefin metathesis catalyst is a Grubbs metathesis catalyst.

12. The method of claim 10 further comprising:
 (c) subjecting the compound of Formula (IVA) or Formula (IV-B) to conditions sufficient to convert $R^4$ to a carboxylic acid group, —COOH to form the compounds of Formula (VI-A) or (VI-B), respectively

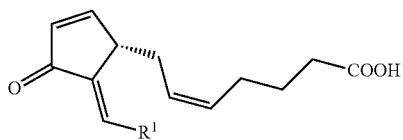

(VI-A)

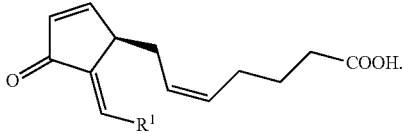

(VI-B)

* * * * *